(12) United States Patent
Kurnik

(10) Patent No.: US 7,680,604 B2
(45) Date of Patent: *Mar. 16, 2010

(54) PCR ELBOW DETERMINATION BY ROTATIONAL TRANSFORM AFTER ZERO SLOPE ALIGNMENT

(75) Inventor: Ronald T. Kurnik, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 901 days.

This patent is subject to a terminal disclaimer.

(21) Appl. No.: 11/349,538

(22) Filed: Feb. 6, 2006

(65) Prior Publication Data

US 2006/0224330 A1    Oct. 5, 2006

Related U.S. Application Data

(63) Continuation-in-part of application No. 11/078,692, filed on Mar. 11, 2005.

(51) Int. Cl.
*G01N 33/48* (2006.01)
*C12P 19/34* (2006.01)

(52) U.S. Cl. .................................. 702/19; 435/91.2
(58) Field of Classification Search ........................ None
See application file for complete search history.

(56) References Cited

U.S. PATENT DOCUMENTS

| | | | |
|---|---|---|---|
| 6,303,305 B1 | 10/2001 | Wittwer et al. | |
| 2006/0204972 A1 | 9/2006 | Kurnik | |
| 2007/0148632 A1 | 6/2007 | Kurnik | |

FOREIGN PATENT DOCUMENTS

| | | |
|---|---|---|
| WO | WO 97/46707 A2 | 12/1997 |
| WO | WO 97/46707 A3 | 12/1997 |
| WO | WO 97/46712 A2 | 12/1997 |
| WO | WO 97/46712 A3 | 12/1997 |
| WO | WO 97/48714 A1 | 12/1997 |

OTHER PUBLICATIONS

Bronshtein and Sendyayev (1997), "Handbook of mathematics," Springer (pp. 196-197).*
Wolovich et al., "The Determination of Implicit Polynomial Canonical Curves," vol. 20 (1998) pp. 1080-1090.*
Wilhelm et al., "SoFar: Software for Fully Automatic Evaluation of Real-Time PCR Data," Biotechniques, vol. 34 (2003) pp. 324-330 and 332.*
Pitas, "Fast Alogrithms for Running Ordering and Max/Min Calculation," IEEE Transactions on Circuits and Systems (1989) vol. 36, pp. 795-804.*
Bar, T., "Kinetic Outlier Detection (KOD) in Real-Time PCR," Nucleic Acids Research, 2003, vol. 31, No. 17, 7 pages.
Bernard, P.S., "Cancer Diagnostics Review, Real-Time PCR Technology for Cancer Diagnostics," Clinical Chemistry, 2002, vol. 48, No. 8, pp. 1178-1185.

Bieche, I. et al., "Quantitation of *MYC* Gene Expression in Sporadic Breast Tumor With a Real-Time Reverse Transcription-PCR assay," *Cancer Research*, Jun. 15, 1999, vol. 59, pp. 2759-2765.
Gibson, U.E.M. et al., "A Novel Method for Real Time Quantitative RT-PCR," *Genome Research*, 1996, vol. 6, pp. 995-1001.
Goll, R. et al., "Evaluation of Absolute Quantitation by Nonlinear Regression in Probe-Based Real-Time PCR," *BMC Bioinformatics*, 2006, vol. 7, No. 107, pp. 1-11.
Higuchi, R., "Kinetic PCR Analysis: Real-Time Monitoring of DNA Amplification Reactions," *Nature Publishing Group*, 1993, vol. 11, pp. 1026-1030.
Kurnik, R.T. et al., "Application of the Mixtures of Experts Algorithm for Signal Processing in a Noninvasive Glucose Monitoring System," *Sensor and Actuators B*, 1999, vol. 60, pp. 19-26.
Lourakis, M.I.A., "A Brief Descritption of the Levenberg-Marquardt Algorithm lmplemened by levmar," Feb. 11, 2005, pp. 1-6.
McLauchlan, P., "Robust Observations," located at <http://gandalf-library.sourceforge.net/tutorial/report/node131.html>, Mar. 17, 2006, last visited on Jan. 25, 2008, 2 pages.
Motulsky, H. et al., *Fitting Models to Biological Data Using Linear and Nonlinear Regression. Version 4.0*, GraphPad Software, Inc., 2003, pp. 3-11 (Table of Contents Only).
Motulsky, H., *Statistics Guide Statistical Analyses for Laboratory and Clinical Researchers, Version 4.0*, GraphPad Software, Inc., Feb. 2005, 6 pages (Table of Contents Only).
Peirson, S. et al., "Experimental Validation of Novel and Conventional Approaches to Quantitative Real-Time PCR Data Analysis," *Nucleic Acids Research*, Oxford University Press, 2003, vol. 31, No. 14, pp. 1-7.
Ramakers, C. et al., "Assumption-Free Analysis of Quantitative Real-Time Polymerase Chain Reaction (PCR) Data," *Neuroscience Letters*, 2003, vol. 339, pp. 62-66.

(Continued)

*Primary Examiner*—John S Brusca
*Assistant Examiner*—Anna Skibinsky
(74) *Attorney, Agent, or Firm*—Townsend and Townsend and Crew LLP; Gerald T. Gray

(57) ABSTRACT

Systems and methods for determining the elbow or Ct value in a real-time, or kinetic, PCR amplification curve data set. A PCR data set may be visualized in a two-dimensional plot of fluorescence intensity vs. cycle number. The data set may be adjusted to have a zero slope. In one aspect, a data set is fit to a double sigmoid curve function with the function parameters determined using a Levenberg-Marquardt regression process. The determined parameters are used to subtract off the linear growth portion from the data set to provide a modified data set. For multiple data sets, all the data curves can be aligned in this manner to have a common baseline slope, e.g., a slope of zero. A rotation transform is applied to a modified data set to rotate the data about a defined coordinate such as the origin so that the data point representing the Ct value becomes a minimum or a maximum along the intensity axis. The data point representing the elbow or Ct value of the curve is identified, and this data point is then rotated back and the cycle number of the data point is returned or displayed.

18 Claims, 17 Drawing Sheets

OTHER PUBLICATIONS

Vu, H.L. et al. "A Method for Quantification of Absolute Amounts of Nucleic Acids by (RT)-PCR and a New Mathematical Model for Data Analysis," *Nucleic Acids Research*, Oxford University Press, 2000, vol. 28, No, 7, pp. 1-9.

Wang, S-S. et al., "Homogeneous Real-Time Detection of Single-Nucleotide Polymorphisms by Strand Displacement Amplification on the BD ProbeTec ET System," *Clinical Chemistry*, 2003, vol. 49, No. 10, pp. 1599-1607.

Weisstein, E., "Cubic Spline," located at <http://mathwolrd.wolfram.com/CubicSpline.html>, 1999, last visited on Jan. 25, 2008, 4 pages.

Weusten, J.J.A.M. et al., "Principles of Quantitation of Viral Loads Using Nucleic Acid Sequence-Based Amplification in Combination With Homogeneous Detection Using Molecular Beacons," *Nucleic Acids Research*, 2002, vol. 30, No. 6, e26, 7 pages.

Whitney, S.E., "Principles of Rapid Polymerase Chain Reactions: Mathematical Modeling and Experimental Verification," *Computational Biology and Chemistry*, 2004, vol. 28, pp. 195-209.

Wilhelm, J., "Validation of an Algorithm for Automatic Quantification of Nucleic Acid Copy Numbers by Real-Time Polymerase Chain Reaction," *Analytical Biochemistry*, 2002, vol. 317, pp. 218-225.

\* cited by examiner

FIG. 5: Spike identification and replacement process flowchart
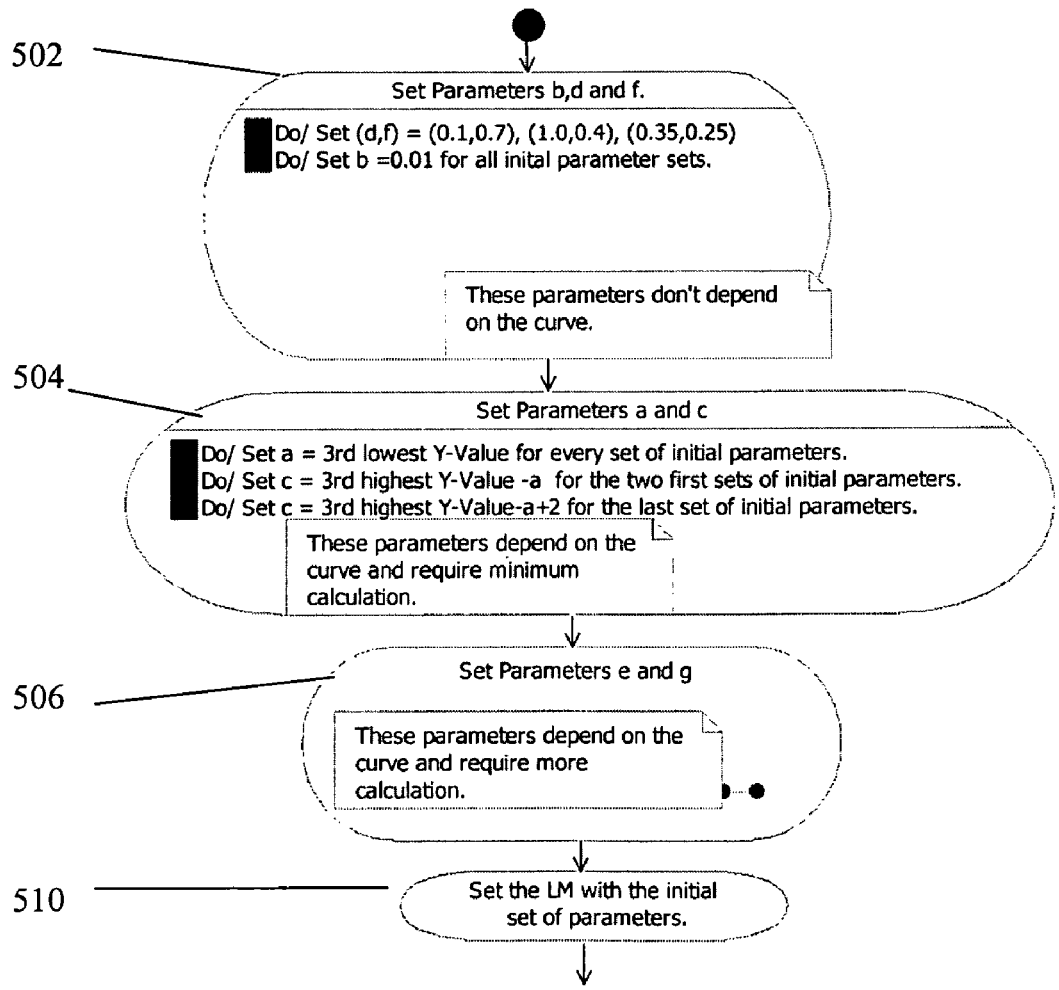

a  constant term
b  linear term
s1 sigmoid 1
s2 sigmoid 2
s  resultant double sigmoid

FIG. 9: Parameter e and g calculation flowchart
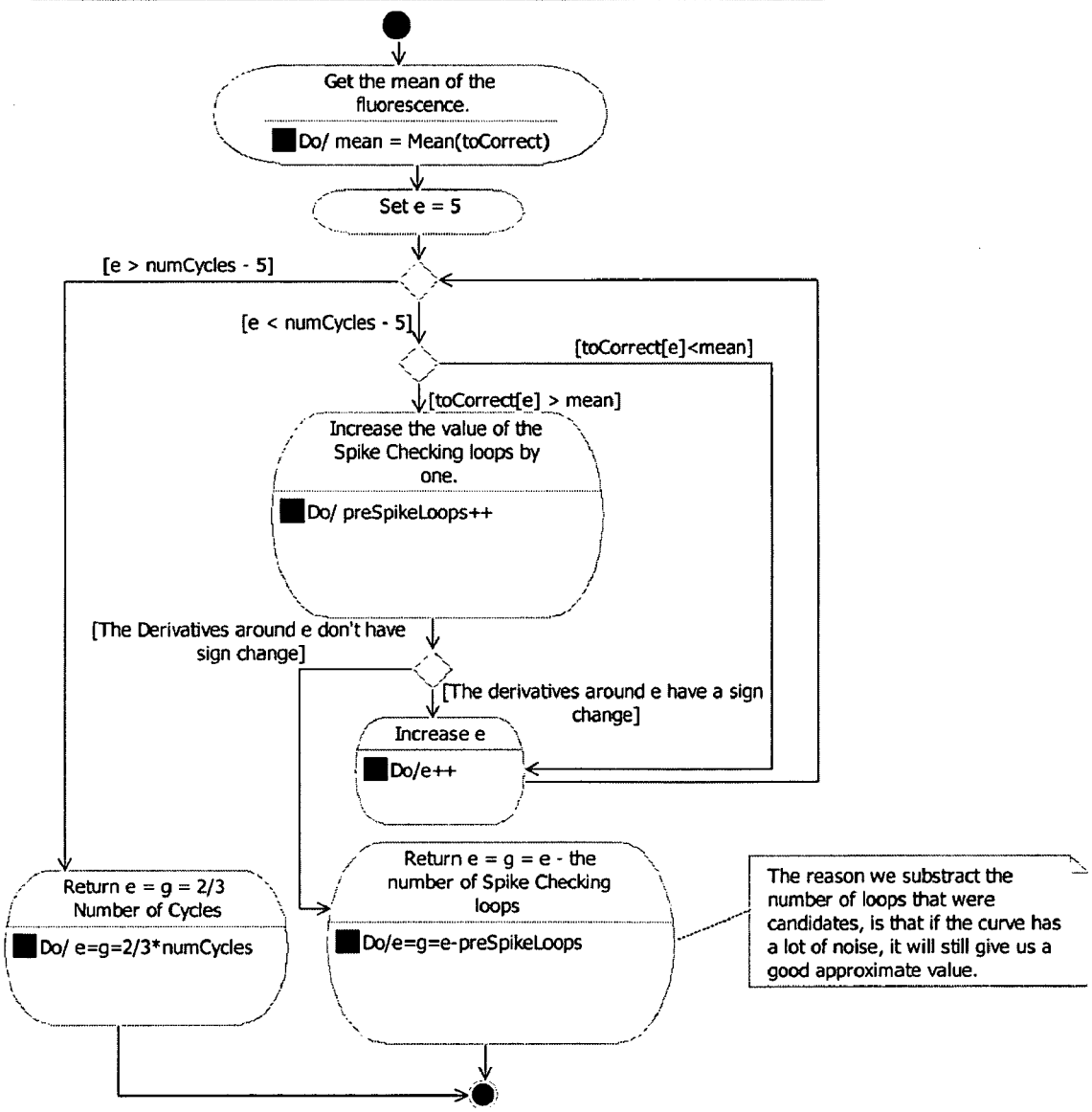

FIG. 10: Levenberg-Marquardt Process flowchart
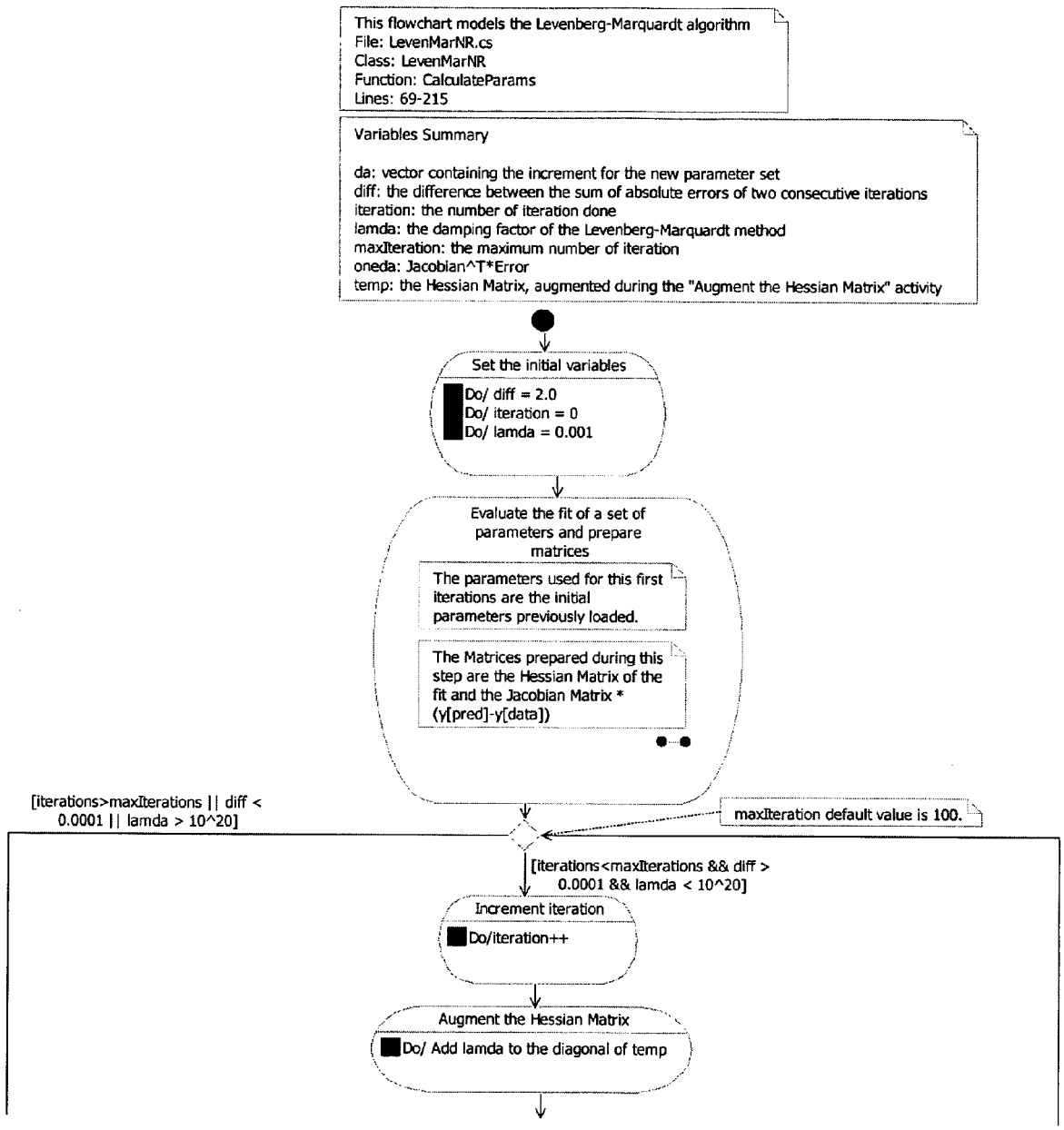

PCR ELBOW DETERMINATION BY ROTATIONAL TRANSFORM AFTER ZERO SLOPE ALIGNMENT

CROSS-REFERENCES TO RELATED APPLICATIONS

This application is a continuation-in-part (CIP) of U.S. application Ser. No. 11/078,692, filed Mar. 11, 2005, titled "Systems and Methods for Determining Real Time PCR Cycle Thresholds Using a Rotation Transformation", which is hereby incorporated by reference in its entirety.

BACKGROUND OF THE INVENTION

The present invention relates generally to systems and methods for processing data representing sigmoid or growth curves, and more particularly to systems and methods for determining characteristic cycle threshold (Ct) or elbow values in PCR amplification curves.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process.

A typical real-time PCR curve is shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which only emit fluorescence signals when they are bound to the target nucleic acid or in certain cases also by means of fluorescent dyes that bind to double-stranded DNA.

For a typical PCR curve, identifying a transition point referred to commonly as the elbow value or cycle threshold (Ct) value is extremely useful for understanding characteristics of the PCR amplification process. The Ct value may be used as a measure of efficiency of the PCR process. For example, typically a defined signal threshold is determined for all reactions to be analyzed and the number of cycles (Ct) required to reach this threshold value is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value 20 in FIG. 1 would be in the region of cycle number 30.

A more precise elbow value in a PCR curve can be determined using several existing methods. For example, various current methods determine the actual value of the elbow as the value where the fluorescence reaches a predetermined level called the AFL (arbitrary fluorescence value). Other current methods might use the cycle number where the second derivative of fluorescence vs. cycle number reaches a maximum. All of these methods have severe drawbacks. For example, some methods are very sensitive to outlier (noisy) data, and the AFL value approach does not work well for data sets with high baselines. Furthermore, these algorithms typically have many parameters (e.g., 50 or more) that are poorly defined, linearly dependent, and often very difficult, if not impossible, to optimize.

Therefore, it is desirable to provide new systems and methods for determining the elbow value in curves, such as sigmoid-type curves, and PCR curves in particular, that overcome these drawbacks and others.

BRIEF SUMMARY OF THE INVENTION

The present invention provides novel, efficient methods for determining characteristic transition values such as elbow values in sigmoid or growth-type curves. In one implementation, the methods of the present invention are particularly useful for determining the cycle threshold (Ct) value in PCR amplification curves.

According to the present invention, a method for determining the elbow or Ct value in a PCR amplification curve data set is provided. The PCR data set may be visualized in a two-dimensional plot of fluorescence intensity vs. cycle number. A rotation transform is applied to the data set to rotate the data about a defined coordinate such as the origin so that the data point representing the Ct value becomes a minimum or a maximum along the intensity axis. The data point representing the elbow or Ct value of the PCR curve is identified. This data point can then be rotated back and the cycle number of the data point returned or displayed.

According to the present invention, a given dataset can be adjusted before rotational transformation processing to have a predefined slope, for example, a zero slope, by subtracting off the linear growth portion as determined by a double sigmoid equation. The double sigmoid equation describes the curve and the parameters of the equation are determined using a Levenberg-Marquardt (LM) regression process or other regression process. In one aspect, outlier or spike points are removed or replaced prior to transformational processing of the dataset. The same or a different regression process can be used to identify and remove or replace the spike points.

According to one aspect of the present invention, a computer-implemented method of determining a specific point of interest in a region of a curve is provided. The method typically includes receiving a data set representing a curve, the data set including a plurality of data points each having a pair of coordinate values, wherein if viewed in a two-dimensional coordinate system the data set has a region of interest, calculating an approximation of the curve by applying a Levenberg-Marquardt (LM) regression process to the data set and a double sigmoid function to determine parameters of the function, and modifying the curve using the determined parameters to produce a modified dataset. The method also typically includes applying a first rotational transformation to at least a portion of the modified data set including the region of interest to produce a transformed data set, identifying a data point in the transformed data set having at least one of a minimum coordinate value or a maximum coordinate value, applying a second rotational transformation, inverse to the first transformation, to the identified data point, and thereafter re-determining at least one coordinate value of the identified data point, wherein the re-determined coordinate value of the identified data point represents a specific point of interest in the curve. In one aspect, the curve is an amplification curve for a kinetic Polymerase Chain Reaction (PCR) process, and the specific point of interest represents the elbow or cycle threshold (Ct) value for the kinetic PCR curve. One or both of the predetermined coordinates of the identify data point are returned or displayed. In certain aspects, modifying includes subtracting off a linear growth portion of the curve.

According to another aspect of the present invention, a computer-implemented method of determining the cycle threshold (Ct) values for a plurality of the Polymerase Chain Reaction (PCR) curves is provided. The method typically includes receiving a plurality of datasets, each data set representing a PCR curve, each data set including a plurality of data points each having a pair of coordinate values, wherein each dataset includes data points in a region of interest which includes the Ct value. The method also typically includes for each dataset, calculating an approximation of the curve by applying a Levenberg-Marquardt (LM) regression process to the data set and a double sigmoid function to determine parameters of the function, modifying the curve using the determined parameters to produce a modified dataset, applying a first rotational transformation to at least a portion of the modified data set including the region of interest to produce a transformed data set, identifying a data point in the transformed data set having at least one of a minimum coordinate value or a maximum coordinate value, applying a second rotational transformation, inverse to the first transformation, to the identified data point, and thereafter re-determining at least one coordinate value of the identified data point, wherein the re-determined coordinate value of the identified data point represents the Ct value for the PCR curve.

According to yet another aspect of the present invention, a computer-readable medium including code for controlling a processor to determine a cycle threshold (Ct) value in a kinetic Polymerase Chain Reaction (PCR) amplification curve is provided. The code typically includes instructions to receive a data set representing a kinetic PCR amplification curve, the data set including a plurality of data points each having a pair of coordinate values, wherein the data set includes data points in a region of interest which includes the Ct value, and instructions to calculate an approximation of the curve by applying a Levenberg-Marquardt (LM) regression process to the data set and a double sigmoid function to determine parameters of the function. The code also typically includes instructions to modify the curve using the determined parameters to produce a modified dataset, apply a first rotational transformation to at least a portion of the modified data set including the region of interest to produce a transformed data set, identify a data point in the transformed data set having at least one of a minimum coordinate value or a maximum coordinate value, apply a second rotational transformation, inverse to the first transformation, to the identified data point; and thereafter re-determine at least one coordinate value of the identified data point, wherein the re-determined coordinate value of the identified data point represents the Ct value for the PCR curve.

According to another aspect of the present invention, a Polymerase Chain Reaction (PCR) system is provided. The PCR system typically includes a kinetic PCR analysis module that generates a PCR data set representing a kinetic PCR amplification curve, the dataset including a plurality of data points each having a pair of coordinate values, wherein the dataset includes data points in the region of interest which includes a cycle threshold (Ct) value. The system also includes an intelligence module adapted to process the PCR data set to determine the Ct value by calculating an approximation of the curve by applying a Levenberg-Marquardt (LM) regression process to the data set and a double sigmoid function to determine parameters of the function and modifying the curve using the determined parameters to produce a modified dataset. The intelligence module is also typically adapted to apply a first rotational transformation to at least a portion of the modified data set including the region of interest to produce a transformed data set, identify a data point in the transformed data set having at least one of a minimum coordinate value or a maximum coordinate value, apply a second rotational transformation, inverse to the first transformation, to the identified data point, and thereafter re-determine at least one coordinate value of the identified data point, wherein the re-determined coordinate value of the identified data point represents the Ct value for the PCR curve.

In certain aspects, the double sigmoid function is of the form $$a + bx + \frac{c}{(1 + \exp^{-d(x-e)})(1 + \exp^{-f(x-g)})},$$

wherein calculating includes iteratively determining one or more of the parameters a, b, c, d, e, f and g of the function.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 9 illustrates a process for determining the value of double sigmoid equation parameters (e) and (g) according to one aspect.

DETAILED DESCRIPTION OF THE INVENTION

Figure 1:
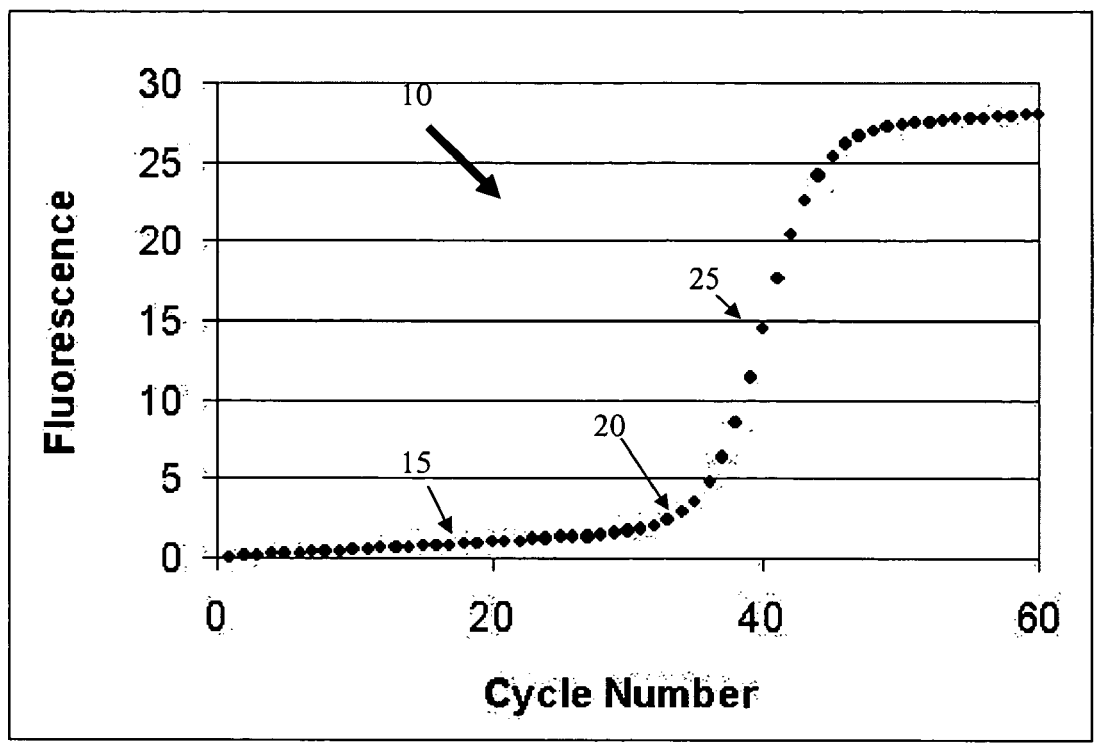
FIG. 1 illustrates an example of a typical PCR growth curve, plotted as fluorescence intensity vs. cycle number.

One example of an amplification curve 10 in the context of a PCR process is shown in FIG. 1. As shown, the curve 10 includes a lag phase region 15, and an exponential phase region 25. Lag phase region 15 is commonly referred to as the baseline or baseline region. Such a curve 10 includes a transitionary region of interest 20 linking the lag phase and the exponential phase regions. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process. In a typical PCR curve, identifying a transition point referred to as the elbow value or cycle threshold (Ct) value is extremely useful for understanding efficiency characteristics of the PCR process. Other processes that may provide similar sigmoid or growth curves include bacterial processes, enzymatic processes and binding processes. In bacterial growth curves, for example, the transition point of interest has been referred to as the time in lag phase, $\theta$. Thus, although the remainder of this document will discuss the invention in terms of its applicability to PCR curves, it should be appreciated that the present invention may be applied to data curves related to these other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, as shown in FIG. 1, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

Figure 2:
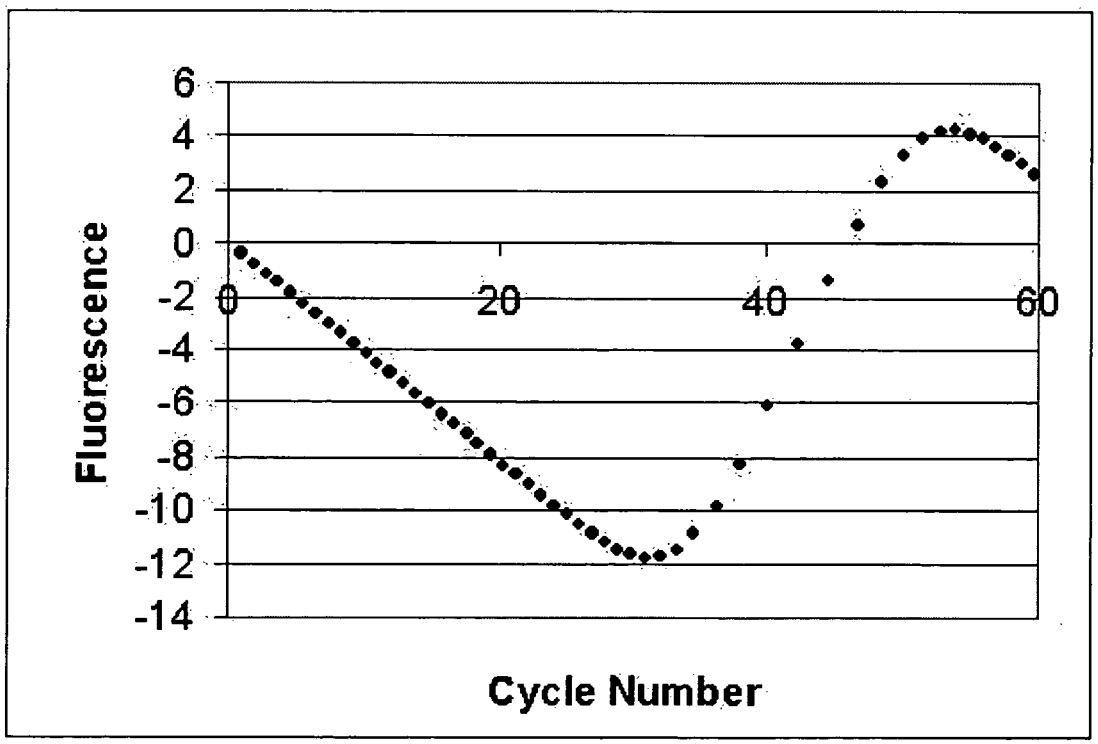
FIG. 2 shows the PCR growth curve data of FIG. 1 rotated by 25 degrees clockwise.
Figure 3:
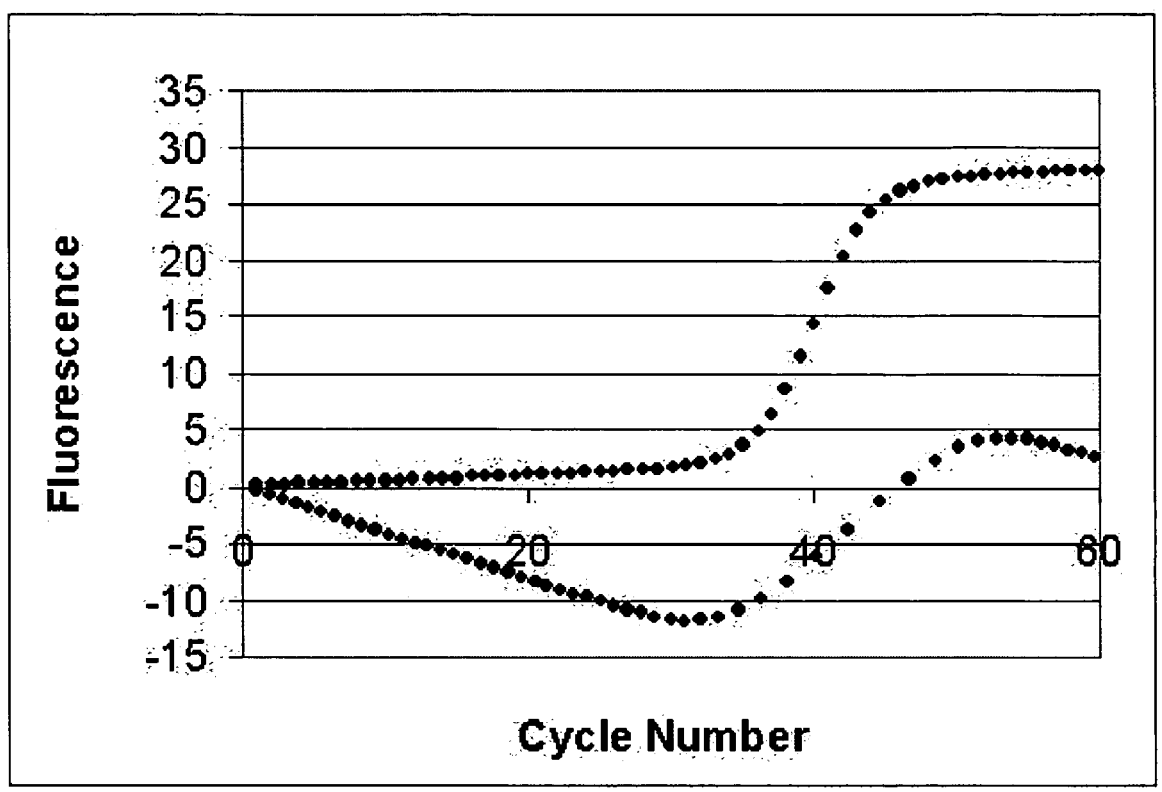
FIG. 3 shows a superposition of FIGS. 1 and 2.

According to the present invention, one embodiment of a process for determining a transitionary value in a single sigmoid curve, such as the elbow value or Ct value of a kinetic PCR amplification curve, can be described briefly as follows. In a first operation, an experimental data set representing the amplification curve (e.g., fluorescence curve in FIG. 1) is acquired. The data set is rotated by an angle theta ($\theta$) so that the rotated data set forms a minimum in the region of the elbow. As an example, FIG. 2 shows the resulting data from FIG. 1 after rotation by 25 degrees clockwise relative to the origin coordinate. FIG. 3 shows a superposition of FIGS. 1 and 2. It is apparent from FIGS. 2 and 3 that by rotating the amplification curve in this manner, the search for the elbow becomes a much simpler task of identifying the location of the minimum in the rotated curve. Any data noise in the region prior to the elbow would have little influence, as the relevant parameter is the minimum in the curve.

In subsequent operations, at least the data point in the transformed data set representing the minimum is rotated back by an angle-theta ($-\theta$), and one or both of the resulting coordinate values (fluorescence and cycle number) representing the elbow or Ct value are output or displayed. In other aspects, additional data points can be interpolated between the experimental data points to provide fractional elbow values as will be described in more detail below. Such interpolation may be performed before or after the first rotational transformation operation.

It should be appreciated that the data set may initially be rotated clockwise or counterclockwise so that the rotated data set forms a minimum or a maximum in the region of the elbow. The subsequent (inverse) rotation transform may then rotate one or more data points in the rotated data set back to the original data set orientation, e.g., counterclockwise or clockwise by the reverse angle. In general, the inverse transform may be performed in any manner that returns the orientation of the data point(s) back to the original visual orientation. Further, the rotation transforms may rotate the data set about any arbitrary line or data point, however rotation about the origin coordinate is preferred.

Figure 4:
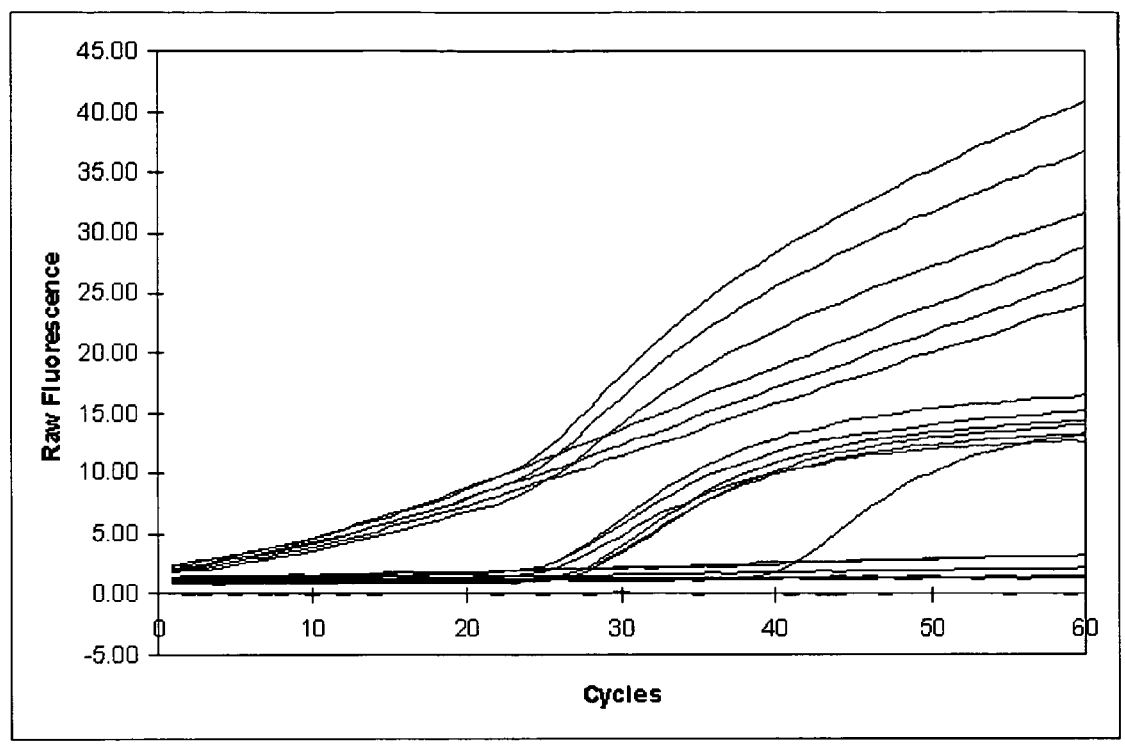
FIG. 4 shows a superposition of multiple PCR curves.

In one aspect, the acquired dataset is processed to remove or modify the baseline slope and provide a modified dataset, which is then rotated as discussed herein. To process certain data sets, it may be advantageous to remove the baseline slope. For example, in a situation where the baseline slopes of a plurality of PCR growth curves take on vastly different values, a single rotation angle may not be suitable for all of the curves. With reference to FIG. 4, which shows multiple PCR data curves, it is clear that a single rotation angle will not satisfy all of the curves. To use a rotational transformation process of the present invention on these datasets, it is advantageous that all of the curves represented by the datasets have a common baseline slope. A slope of zero would be most advantageous. Therefore, according to one embodiment of the present invention, a process for determining and modifying or removing the baseline slope of the dataset is provided. According to this embodiment, a regression process such as a Levenberg-Marquardt regression process is used to determine the parameters of a double sigmoid equation that defines a typical PCR or growth curve. The double sigmoid equation provides a mechanism whereby all the curves can be lined up to a predefined slope, for example, a zero slope. After the parameters of the equation have been determined, the dataset can be adjusted to have a zero slope by subtracting off the linear growth portion of the double sigmoid equation.

Figure 5:
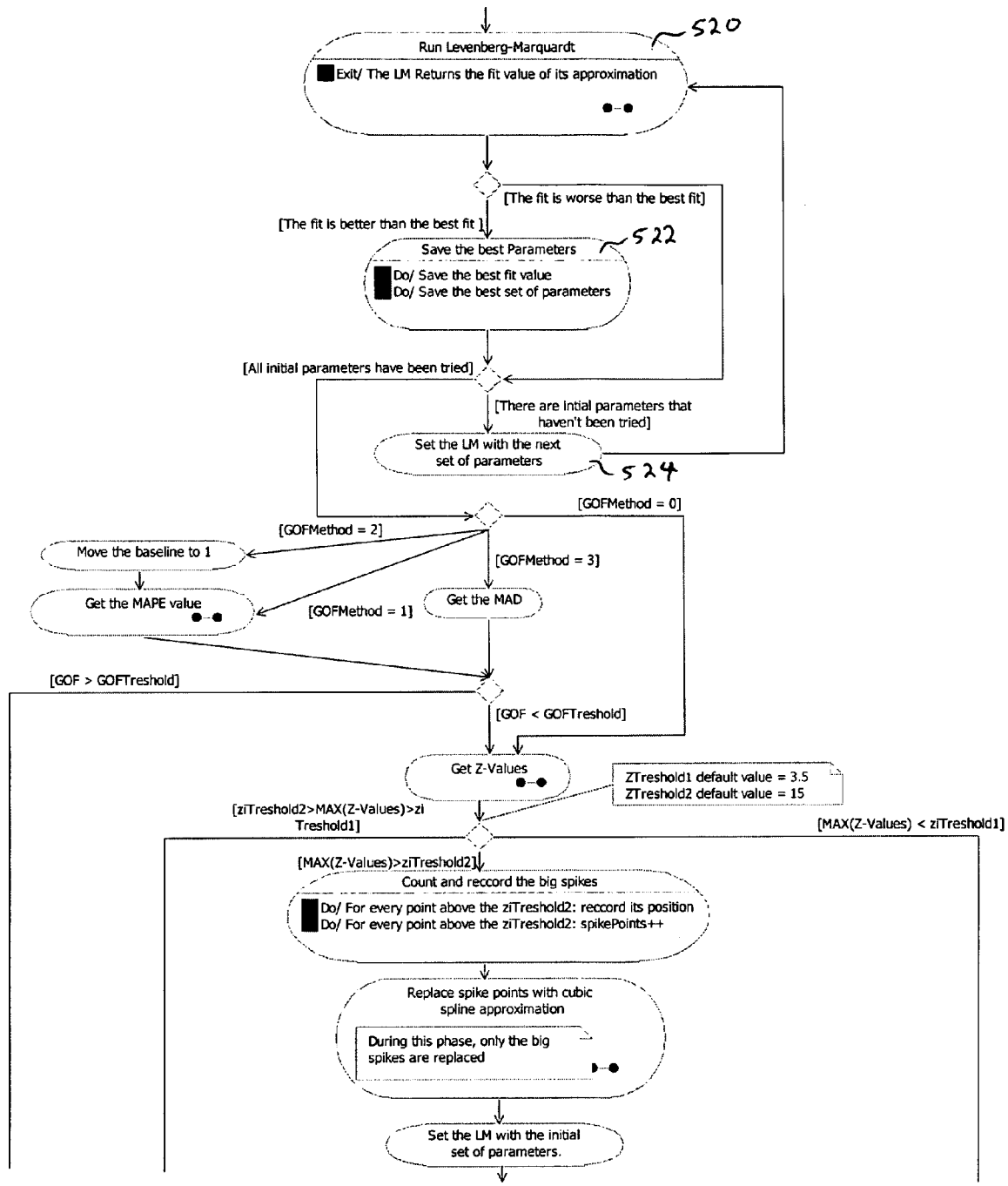
FIG. 5 illustrates a more detailed process flow for a spike identification and replacement process according to one embodiment of the present invention.
Figure 5:
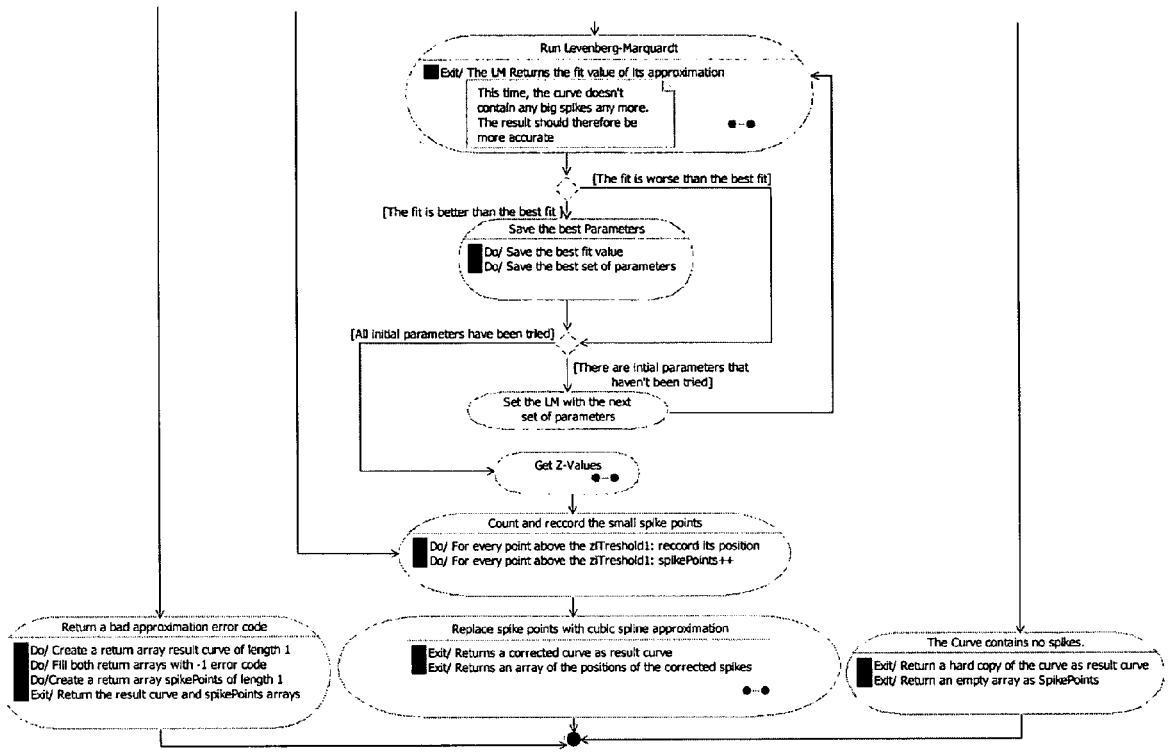

In certain aspects, outlier or spike points in the dataset are removed or replaced prior to rotational transformation processing. FIG. 5 illustrates the process flow for identifying and replacing spike points in datasets representing a PCR or other growth curves. A more detailed description of the process for determining and removing or replacing spike points, according to this aspect can be found in U.S. patent application Ser. No. 11/316,315, titled "Levenberg Marquardt Outlier Spike Removal Method," filed on Dec. 20, 2005, the disclosure of which incorporated by reference in its entirety.

LM Regression Process

Steps 502 through 524 of FIG. 5 also illustrate a process flow for determining the parameters of a fit function. These parameters can be used in modifying or removing the baseline slope of the data set representing a sigmoid or growth type curve such as a PCR curve according to one embodiment of the present invention. Where the dataset has been processed to produce a modified dataset with removed or replaced spike points, the modified spikeless dataset may be processed according to steps 502 through 524 to identify the parameters of the fit function.

In one embodiment as shown, a Levenberg-Marquardt (LM) method is used to calculate a robust curve approximation of a data set. The LM method is a non-linear regression process; it is an iterative technique that minimizes the distance between a non-linear function and a data set. The process behaves like a combination of a steepest descent process and a Gauss-Newton process: when the current approximation doesn't fit well it behaves like the steepest descent process (slower but more reliable convergence), but as the current approximation becomes more accurate it will then behave like the Gauss-Newton process (faster but less reliable convergence). The LM regression method is widely used to solve non-linear regression problems.

In general, the LM regression method includes an algorithm that requires various inputs and provides output. In one aspect, the inputs include a data set to be processed, a function that is used to fit the data, and an initial guess for the parameters or variables of the function. The output includes a set of parameters for the function that minimizes the distance between the function and the data set.

According to one embodiment, the fit function is a double sigmoid of the form:

$$a + bx + \frac{c}{(1 + \exp^{-d(x-e)})(1 + \exp^{-f(x-g)})}. \quad (1)$$

The choice of this equation as the fit function is based on its flexibility and its ability to fit the different curve shapes that a typical PCR curve or other growth curve may take. One skilled in the art will appreciate that other fit functions may be used as desired.

Figure 6:
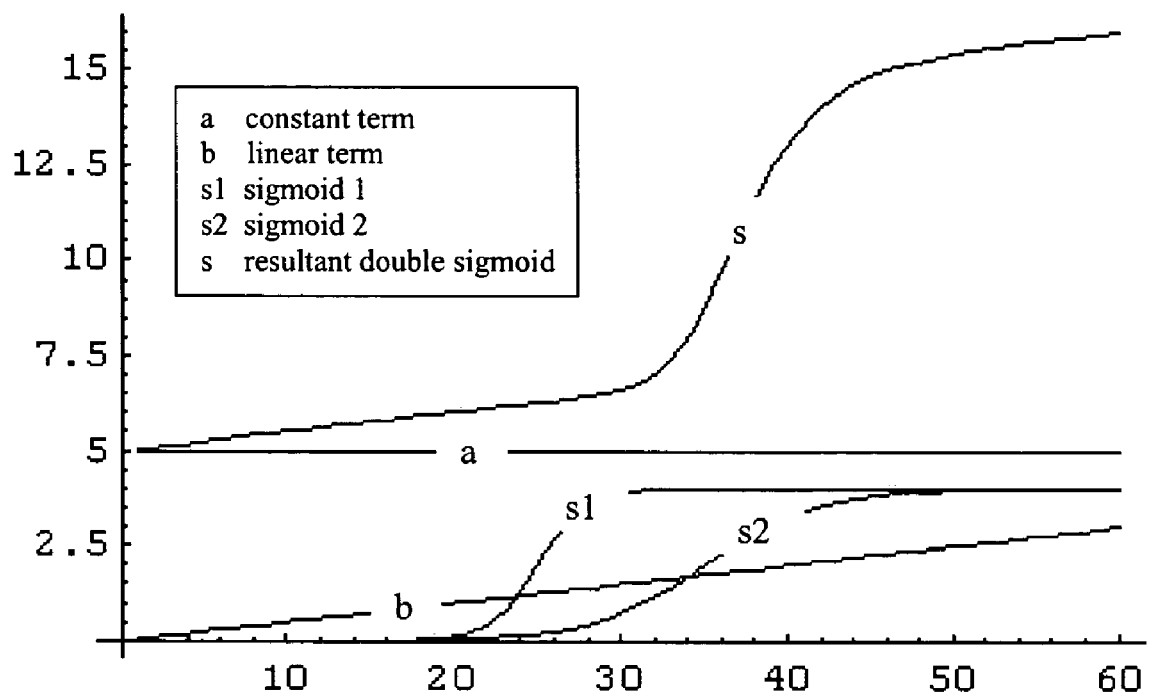
FIG. 6 illustrates a decomposition of the double sigmoid equation including parameters a-g.
Figure 7:
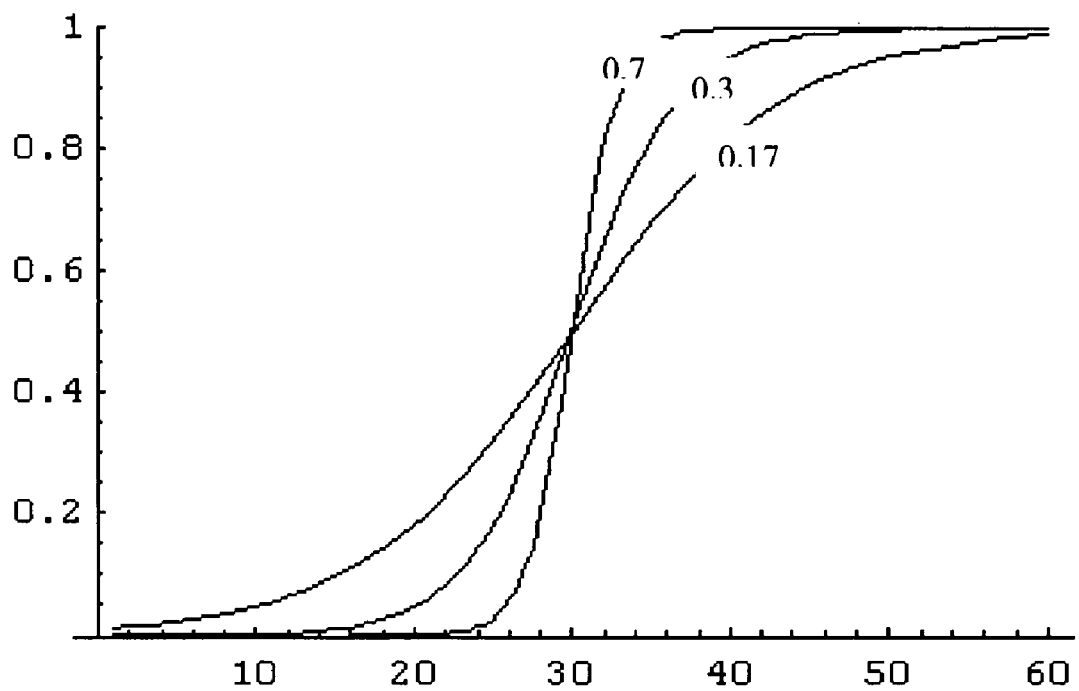
FIG. 7 shows the influence of parameter (d) on the curve and the position of (e), the x value of the inflexion point.

The double sigmoid equation (1) has 7 parameters: a, b, c, d, e, f and g. The equation can be decomposed into a sum of a constant, a slope and a double sigmoid. The double sigmoid itself is the multiplication of two sigmoids. FIG. 6 illustrates a decomposition of the double sigmoid equation (1). The parameters d, e, f and g determine the shape of the two sigmoids. To show their influence on the final curve, consider the single sigmoid:

$$\frac{1}{1 + \exp^{-d(x-e)}}, \quad (2)$$

where the parameter d determines the "sharpness" of the curve and the parameter e determines the x-value of the inflexion point. FIG. 7 shows the influence of the parameter d on the curve and of the parameter e on the position of the x value of the inflexion point. Table 1, below, describes the influence of the parameters on the double sigmoid curve.

TABLE 1

Double sigmoid parameters description

| Parameter | Influence on the curve |
|---|---|
| a | Value of y at x = 0 |
| b | baseline and plateau slope |
| c | AFI of the curve |
| d | "sharpness" of the first sigmoid (See FIG. 7) |
| e | position of the inflexion point of the first sigmoid (See FIG. 7) |

TABLE 1-continued

Double sigmoid parameters description

| Parameter | Influence on the curve |
|---|---|
| f | "sharpness" of the second sigmoid |
| g | position of the inflexion point of the second sigmoid |

In one aspect, the "sharpness" parameters d and f of the double sigmoid equation should be constrained in order to prevent the curve from taking unrealistic shapes. Therefore, in one aspect, any iterations where d<−1 or d >1.1 or where f<−1 or f>1.1 is considered unsuccessful. In other aspects, different constraints on parameters d and f may be used.

Figure 8:
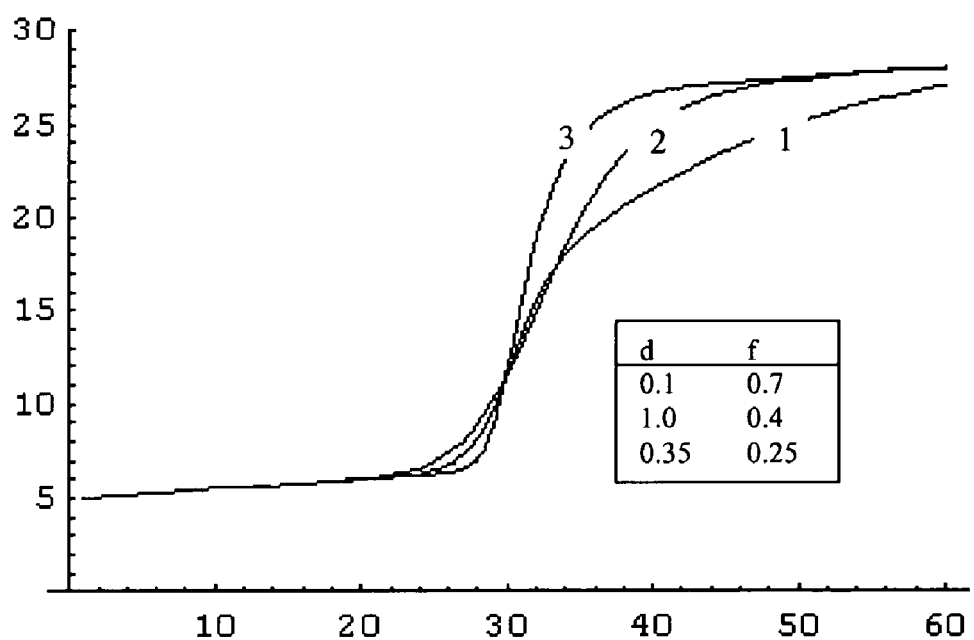
FIG. 8 shows an example of the three curve shapes for the different parameter sets.

Because the Levenberg-Marquardt algorithm is an iterative algorithm, an initial guess for the parameters of the function to fit is typically needed. The better the initial guess, the better the approximation will be and the less likely it is that the algorithm will converge towards a local minimum. Due to the complexity of the double sigmoid function and the various shapes of PCR curves or other growth curves, one initial guess for every parameter may not be sufficient to prevent the algorithm from sometimes converging towards local minima. Therefore, in one aspect, multiple (e.g., three or more) sets of initial parameters are input and the best result is kept. In one aspect, most of the parameters are held constant across the multiple sets of parameters used; only parameters c, d and f may be different for each of the multiple parameter sets. FIG. 8 shows an example of the three curve shapes for the different parameter sets. The choice of these three sets of parameters is indicative of three possible different shapes of curves representing PCR data. It should be understood that more than three sets of parameters may be processed and the best result kept.

As shown in FIG. 5, the initial input parameters of the LM method are identified in step 510. These parameters may be input by an operator or calculated. According to one aspect, the parameters are determined or set according to steps 502, 504 and 506 as discussed below.

Calculation of Initial Parameter (a):

The parameter (a) is the height of the baseline; its value is the same for all sets of initial parameters. In one aspect, in step 504 the parameter (a) is assigned the 3rd lowest y-axis value, e.g., fluorescence value, from the data set. This provides for a robust calculation. In other aspects, of course, the parameter (a) may be assigned any other fluorescence value as desired such as the lowest y-axis value, second lowest value, etc.

Calculation of Initial Parameter (b):

The parameter (b) is the slope of the baseline and plateau. Its value is the same for all sets of initial parameters. In one aspect, in step 502 a static value of 0.01 is assigned to (b) as ideally there shouldn't be any slope. In other aspects, the parameter (b) may be assigned a different value, for example, a value ranging from 0 to about 0.5.

Calculation of Initial Parameter (c):

The parameter (c) represents the absolute intensity of the curve; for PCR data the parameter (c) typically represents the AFI of the curve. To calculate the AFI, the height of the plateau is important. To calculate this in a robust way, in one aspect, the 3rd highest y-axis value, e.g., fluorescence value, is assigned as the plateau height in step 504. Then, the AFI=height of plateau−height of baseline=3rd highest fluorescence value−(a). In other aspects, the parameter (c) may be assigned any other fluorescence value as desired, such as the highest y-axis value, next highest, etc.

As shown in FIG. 8, for the last two sets of parameters, c=AFI. For the first set of parameters, c=AFI+2. This change is due to the shape of the curve modeled by the first set of parameters, which doesn't have a plateau.

Calculation of Parameters (d) and (f):

The parameters (d) and (f) define the sharpness of the two sigmoids. As there is no way of giving an approximation based on the curve for these parameters, in one aspect three static representative values are used in step 502. It should be a. that point does not lie near the beginning, e.g., within the first 5 cycles, of the curve;
b. that point does not lie near the end, e.g., within the 5 last cycles, of the curve; and
c. the derivatives around the point (e.g., in a radius of 2 points around it) do not show any change of sign. If they do, the point is likely to be a spike and should therefore be rejected.

Table 3, below, shows examples of initial parameter values as used in FIG. 8 according to one aspect.

TABLE 3

Initial parameters values:

| | Initial parameter set number | | |
|---|---|---|---|
| | 1 | 2 | 3 |
| Value of a | $3^{rd}$ lowest fluorescence value | $3^{rd}$ lowest fluorescence value | $3^{rd}$ lowest fluorescence value |
| Value of b | 0.01 | 0.01 | 0.01 |
| Value of c | $3^{rd}$ highest fluorescence value - a + 2 | $3^{rd}$ highest fluorescence value - a | $3^{rd}$ highest fluorescence value - a |
| Value of d | 0.1 | 1.0 | 0.35 |
| Value of e | X of the first non-spiky point above the mean of the fluorescence | X of the first non-spiky point above the mean of the fluorescence | X of the first non-spiky point above the mean of the fluorescence |
| Value of f | 0.7 | 0.4 | 0.25 |
| Value of g | X of the first non-spiky point above the mean of the fluorescence | X of the first non-spiky point above the mean of the fluorescence | X of the first non-spiky point above the mean of the fluorescence | understood that other static or non-static values may be used for parameters (d) and/or (f). These pairs model the most common shapes on PCR curves encountered. Table 2, below, shows the values of (d) and (f) for the different sets of parameters as shown in FIG. 8.

TABLE 2

Values of parameters d and f

| Parameter set number | Value of d | Value of f |
|---|---|---|
| 1 | 0.1 | 0.7 |
| 2 | 1.0 | 0.4 |
| 3 | 0.35 | 0.25 |

Calculation of Parameters (e) and (g):

In step 506, the parameters (e) and (g) are determined. The parameters (e) and (g) define the inflexion points of the two sigmoids. In one aspect, they both take the same value across all the initial parameter sets. Parameters (e) and (g) may have the same or different values. To find an approximation, in one aspect, the x-value of the first point above the mean of the intensity, e.g., fluorescence, (which isn't a spike) is used. A process for determining the value of (e) and (g) according to this aspect is shown in FIG. 9 and discussed below. A more detailed description of the process for determining the value of the parameters (e) and (g), and others, according to this aspect can be found in U.S. patent application Ser. No. 11/316,315, filed on Dec. 20, 2005, the disclosure of which was previously incorporated by reference in its entirety.

With reference to FIG. 9, initially, the mean of the curve (e.g., fluorescence intensity) is determined. Next, the first data point above the mean is identified. It is then determined whether:

Returning to FIG. 5, once all the parameters are set in step 510, a LM process 520 is executed using the input data set, function and parameters. Traditionally, the Levenberg-Marquardt method is used to solve non-linear least-square problems. The traditional LM method calculates a distance measure defined as the sum of the square of the errors between the curve approximation and the data set. However, when minimizing the sum of the squares, it gives outliers an important weight as their distance is larger than the distance of non-spiky data points, often resulting in inappropriate curves or less desirable curves. Therefore, according to one aspect of the present invention, the distance between the approximation and the data set is computed by minimizing the sum of absolute errors as this does not give as much weight to the outliers. In this aspect, the distance between the approximation and data is given by:

$$\text{distance} = \Sigma |y_{data} - y_{approximation}|. \qquad (3)$$

As above, in one aspect, each of the multiple (e.g., three) sets of initial parameters are input and processed and the best result is kept as shown in steps 522 and 524, where the best result is the parameter set that provides the smallest or minimum distance in equation (1). In one aspect, most of the parameters are held constant across the multiple sets of parameters; only c, d and f may be different for each set of parameters. It should be understood that any number of initial parameter sets may be used.

Figure 10:
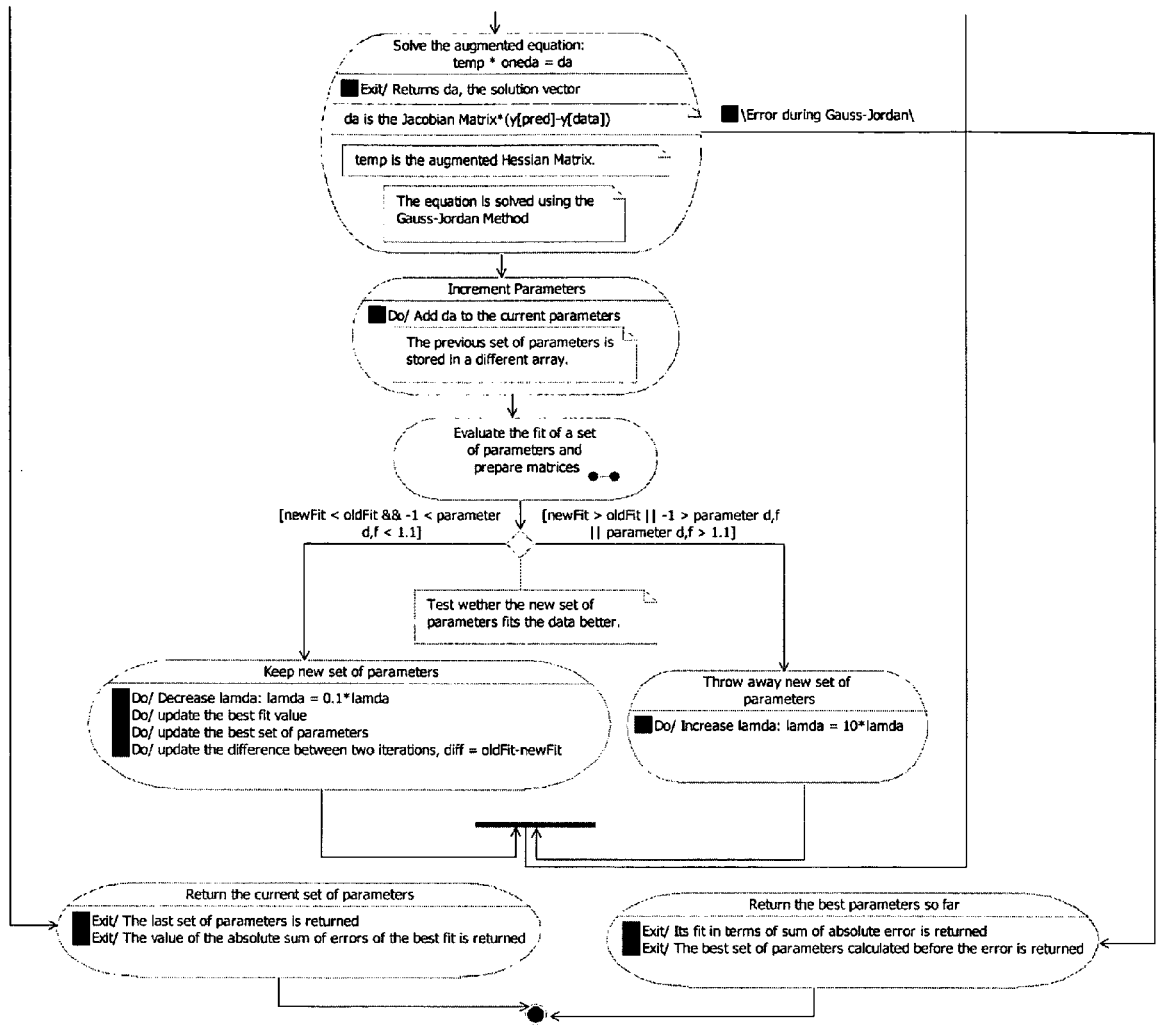
FIG. 10 illustrates a process flow of Levenberg-Marquardt process for an initial set of parameters.

FIG. 10 illustrates a process flow of LM process 520 for a set of parameters according to the present invention. As explained above, the Levenberg-Marquardt method can behave either like a steepest descent process or like a Gauss-Newton process. Its behavior depends on a damping factor $\lambda$. The larger $\lambda$ is, the more the Levenberg-Marquardt algorithm will behave like the steepest descent process. On the other hand, the smaller $\lambda$ is, the more the Levenberg-Marquardt algorithm will behave like the Gauss-Newton process. In one aspect, λ is initiated at 0.001. It should be appreciated that λ may be initiated at any other value, such as from about 0.000001 to about 1.0.

As stated before, the Levenberg-Marquardt method is an iterative technique. According to one aspect, as shown in FIG. 10 the following is done during each iteration:
1. The Hessian Matrix (H) of the precedent approximation is calculated.
2. The transposed Jacobian Matrix ($J^T$) of the precedent approximation is calculated.
3. The distance vector (d) of the precedent approximation is calculated.
4. The Hessian Matrix diagonal is augmented by the current damping factor λ:

$$H_{aug} = H\lambda \quad (4)$$

5. Solve the augmented equation:

$$H_{aug} x = J^T d \quad (5)$$

6. The solution x of the augmented equation is added to the parameters of the function.
7. Calculate the distance between the new approximation and the curve.
8. If the distance with this new set of parameters is smaller than the distance with the previous set of parameters:
   The iteration is considered successful.
   Keep or store the new set of parameters.
   Decrease the damping factor λ, e.g., by a factor 10.
   If the distance with this new set of parameters is larger than the distance with the previous set of parameters:
   The iteration is considered unsuccessful.
   Throw away the new set of parameters.
   Increase the damping factor λ, e.g., by a factor of 10.

In one aspect, the LM process of FIG. 10 iterates until one of the following criteria is achieved:
1. It has run for a specified number, N, of iterations. This first criterion prevents the algorithm from iterating indefinitely. For example, in one aspect as shown in FIG. 10, the default iteration value N is 100. 100 iterations should be plenty for the algorithm to converge if it can converge. In general, N can range from fewer than 10 to 100 or more.
2. The difference of the distances between two successful iterations is smaller than a threshold value. e.g., 0.0001. When the difference becomes very small, the desired precision has been achieved and continuing to iterate is pointless as the solution won't become significantly better.
3. The damping factor λ exceeds a specified value, e.g., is larger than $10^{20}$. When λ becomes very large, the algorithm won't converge any better than the current solution, therefore it is pointless to continue iterating. In general, the specified value can be significantly smaller or larger than $10^{20}$.

After the parameters have been determined, the dataset may be adjusted to have zero slope by subtracting out the linear growth portion of the curve. Mathematically, $$dataNew = data - (a+bx), \quad (6)$$

where dataNew is the data set (data) with the linear growth of baseline slope removed, a and b are the parameter values determined by using the LM equation to regress the curve, and x is the cycle number. Thus, for every data value along the x-axis, the constant a and the slope b times the x value is subtracted from the data to produce a data curve with a zero slope. In certain aspects, spike points are removed from the dataset prior to rotational transformation processing.

In another aspect, the dataset may be adjusted to have zero slope according to the following equation:

$$dataNew = (data - (a+bx))/a. \quad (7)$$

One skilled in the art will appreciate that other equations may be used to modify the baseline using the parameters as determined by the Levenberg-Marquardt or other regression process.

Figure 11:
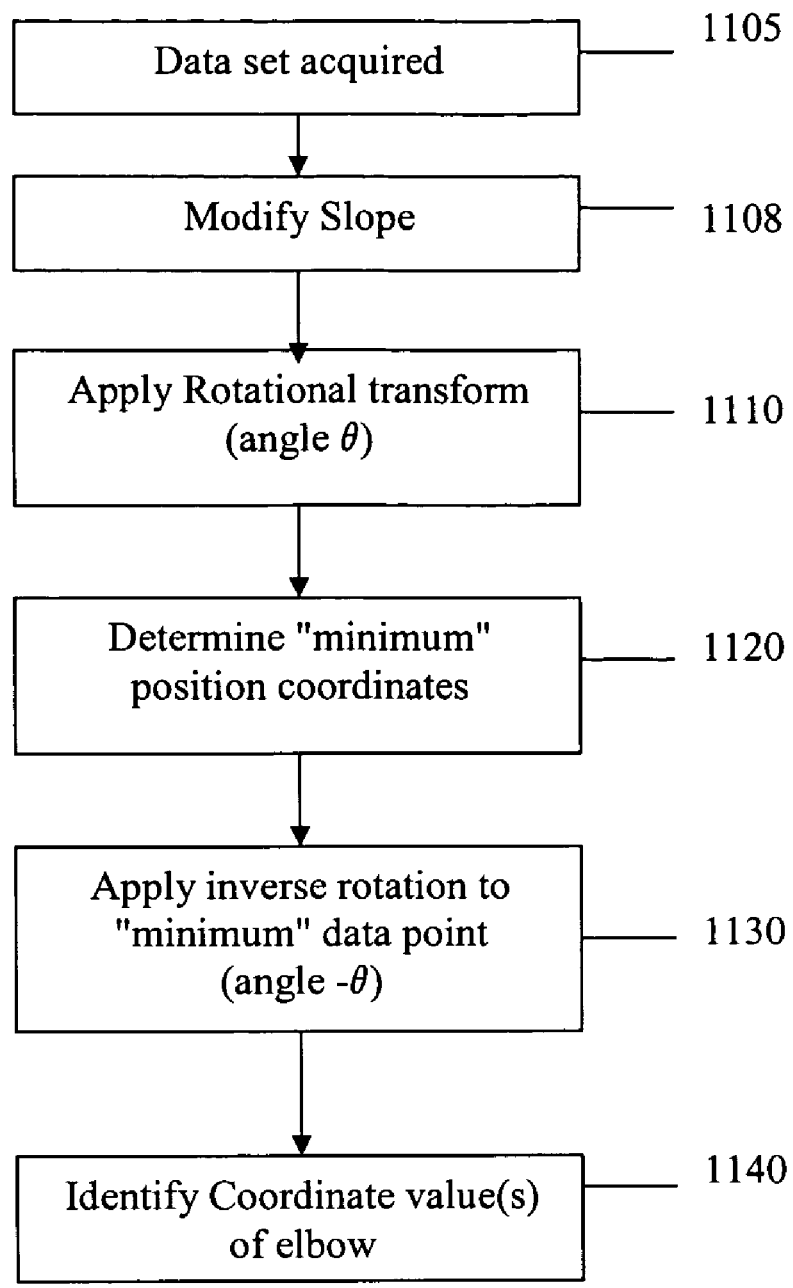
FIG. 11 illustrates a process for determining the elbow value for a PCR process according to one embodiment.

A process for determining the elbow value in a kinetic PCR curve according to one embodiment is shown in FIG. 11. In step 1105, the data set is acquired. In the case where the determination process is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the module after the experiment has been completed. Similarly, the data set may be provided to a separate system such as a desktop computer system via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. After a data set has been received or acquired, in step 1108 the baseline slope is modified. For example, the baseline may be set to zero slope by determining the parameters of a double signal in equation using the Levenberg-Marquardt process described above, and using those parameters to subtract off the baseline slope. Additionally, spike points may be removed from the dataset prior to step 1108 as described with reference to FIG. 5. For example, the dataset acquired in step 1105 can be a dataset with spikes already removed. In step 1110 a rotational transformation is applied to at least a portion of the modified data set containing the elbow, so as to rotate the data set by an angle theta (θ). In step 1120, the minimum position coordinate in the rotated data set is determined. In step 1130, an inverse rotation transformation of this point is performed by rotating in the opposite direction by the angle –θ to give the final coordinates of the elbow. It should be appreciated that other data points, in addition to the "minimum" data point determined in step 1120, may be rotated in step 1130. In step 1140, one or both of the re-determined coordinate values of the identified elbow point are returned, e.g., output or displayed. The following example illustrates the process: In FIG. 2 (rotated data set), the minimum point is at coordinates (30.92,-11.79). This point is then rotated by –25 degrees (counter-clockwise) to give the final coordinates of (33.0, 2.38). Thus, the elbow is determined to be 33.0 (cycle number).

In one preferred aspect, each rotation transformation rotates the data points about the origin (0,0), however, the data may be rotated about any coordinate as desired. Additionally, the data set may initially be rotated in a different manner, for example counterclockwise by an angle –(180°–θ) or clockwise by an angle (180°+θ) in step 110. In this case, the relevant determination in step 120 is to determine the "maximum" value. Thus, it should be appreciated by one skilled in the art that other rotational transform parameters will allow for identification of the elbow value.

Figure 12:
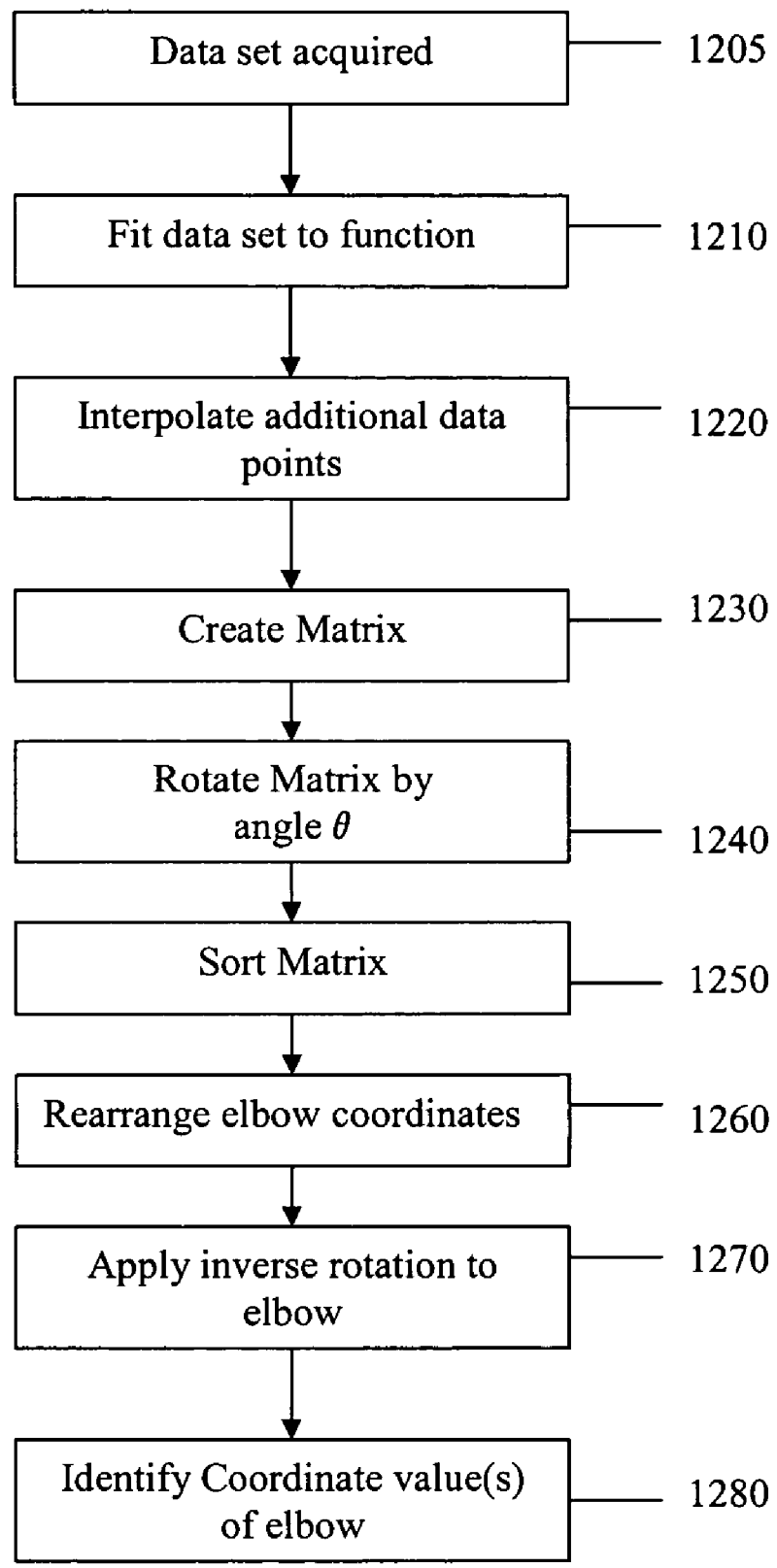
FIG. 12 illustrates a process for determining the elbow value for a PCR process according to another embodiment.

A process for determining the elbow value in a kinetic PCR process according to another embodiment is shown in FIG. 12. After the data set has been received or acquired in step 1205, in step 1210 a dataset is processed to 1) fit it to the double sigmoid equation and determine the parameters of the equation according to the Levenberg Marquardt process described above, and 2) modify the baseline slope as desired, e.g., set the slope to zero. In step 1210, another function such as a cubic spline function may be fit to all or a portion of the data points. For example, where the dataset acquired in step 1205 has already been fit to the double sigmoid equation using a Levenberg-Marquardt process, has already had its baseline modified, or otherwise need not be fit to double sigmoid equation, another fit function such as a spline function may be used. This may be done using the software application Mathematica® or other application. In optional step 1220, data points are interpolated between existing data points at cycle intervals of 1.0 or less, e.g., 0.05 or 0.01 using the fit function, e.g., using the double sigmoid function, a spline function or other fit function. In step 1230, a matrix of data points (x,y) is created of the (interpolated fluorescence, cycle numbers). This large matrix of numbers, or a portion thereof, is then rotated by an angle theta (θ) in step 1240 and coordinates are exchanged to give coordinates (y',x'). In step 1250, this (rotated) matrix is sorted in ascending order of fluorescence values. In this manner, the data point having the minimum fluorescence value is determined by identifying the data point in the first position. The (y',x') coordinates of the first position in the sorted matrix corresponds to the rotated elbow. In step 1260, this minimum (y',x') is then rearranged as (x',y') and in step 1270, the inverse rotation of this single point by angle-theta (−θ) is performed to give the elbow value. It should be appreciated that the inverse rotation may be applied to additional points near this single point. Also, as above, it should be understood that interpolation of additional data points (optional step 1220) may be performed before or after application of the rotational transformation in step 1240. Further, as above, different rotational angles and directions may be used, and sorting may be used to identify a "maximum" where appropriate. In step 1280, one or both of the coordinate values of the elbow point are returned, e.g., output or displayed.

It should be appreciated that the Ct determination processes may be implemented in computer code running on a processor of a computer system. The code includes instructions for controlling a processor to implement various aspects and steps of the Ct determination processes. The code is typically stored on a hard disk, RAM or portable medium such as a CD, DVD, etc. Similarly, the processes may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

One skilled in the art should appreciate that the elbow determination processes of the present invention can be coded using a variety of programming languages such as C, C++, C#, Fortran, VisualBasic, etc., as well as applications such as Mathematica which provide pre-packaged routines, functions and procedures useful for data visualization and analysis. Another example of the latter is MATLAB®.

An example of Mathematica code configured to perform rotation transformation process operations on a vector yd of fluorescence values for a single data set is shown below:

```
Needs ["Geometry 'Rotations'"]
CtRot[yd_,theta_]:=Module[{data,vec,ni,rotp,x,y,rt},
    data=Table[{i,yd[[i]]},{i,1,Length[yd]}];
    vec=Table[{i,1},{i,1,Length[data]}];
```

-continued

```
    For[i=1,i<=Length[data],i++,
        vec[[i]]=Rotate2D[{data[[i,1]],data[[i,2]]},theta Degree,{0,0}]
    ];
IntF=Interpolation[vec];
mind=Ceiling[vec[[1]][[1]]];
maxd=Floor[vec[[Length[vec]]][[1]]];
rotp2=Sort[Table[{IntF[x],x},{x,mind,maxd,0.01}]][[1]];
rotp={rotp2[[2]],rotp2[[1]]};
rt=Rotate2D[rotp,-theta Degree,{0,0}];
rt[[1]]]
```

Figure 13A:
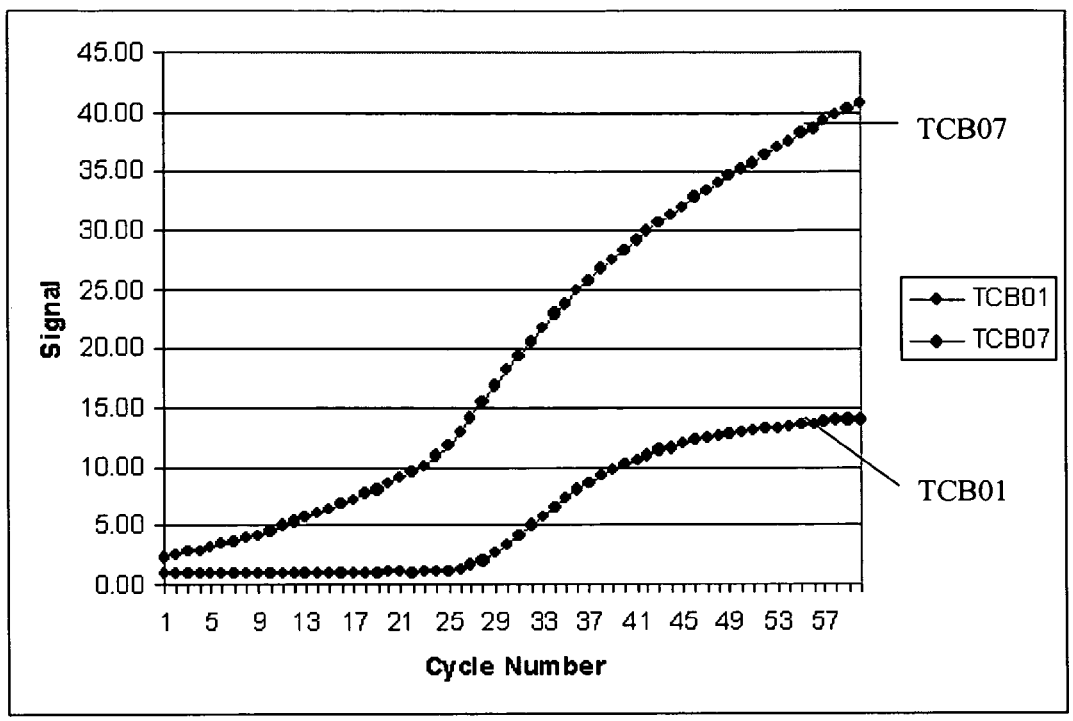
FIG. 13 shows an example of a) a plot of two data sets for two amplification curves, and b) the two data sets processed to modify the baselines according to the present invention.
Figure 13B:
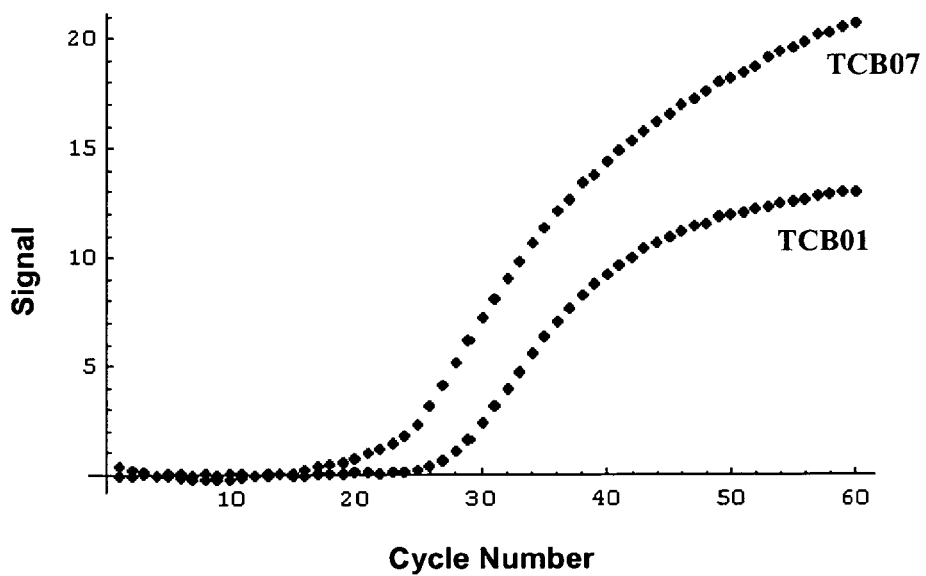

FIG. 13 shows an example of a) a plot of two data sets for two amplification curves, and b) the two data sets processed to modify the baselines according to the present invention. It is clear that the optimum rotation angle for curve TCB01 will be different than that for curve TCB07. A reasonable angle to use for curve TCB01 is 15 degrees. The resultant Ct values for both curves, using the a single rotation at 15 degrees, gives Ct values of:

| Curve | Ct Value |
|---|---|
| TCB01 | 26.9 |
| TCB07 | undefined |

The Ct Value for curve TCB07 is undefined, because at an angle of 15 degrees, the rotated curve has no minimum. When equation (4) is used to subtract out the linear growth from both of the data sets, the two curves in FIG. 13*a* become those shown in FIG. 13*b*. When the rotation algorithm is then applied to each of these data sets, using the same angle of 15 degrees, the Ct values are found to be:

| Curve | Ct Value |
|---|---|
| TCB01 | 26.9 |
| TCB07 | 22.9 |

Rotation Angle Optimization

According to one embodiment, a methodology to optimize the rotation transforms applied, for example, in steps 1110 (FIG. 11) and 1240 (FIG. 12), is provided. According to one aspect, optimization of the rotation angle θ is performed by minimization of the Coefficient of Variation (Cv) of Ct values predicted at target titer values.

The rotation transform algorithm described above uses a single parameter of rotation angle (θ) to determine the Ct (elbow) in kinetic PCR. This algorithm thus provides a framework where the quality of the parameter fit can be optimized. According to the present invention, the problems associated with optimizing parameters associated with other methodologies are advantageously eliminated by optimizing the single parameter that this algorithm uses: rotation angle. In one aspect, this is done by providing a rigorous mathematical method to optimize the rotation angle. In particular, according to one aspect of the present invention the coefficient of variation (Cv) of Ct values at target titer values is minimized to provide an optimal rotation angle. An example follows.

Figure 14:
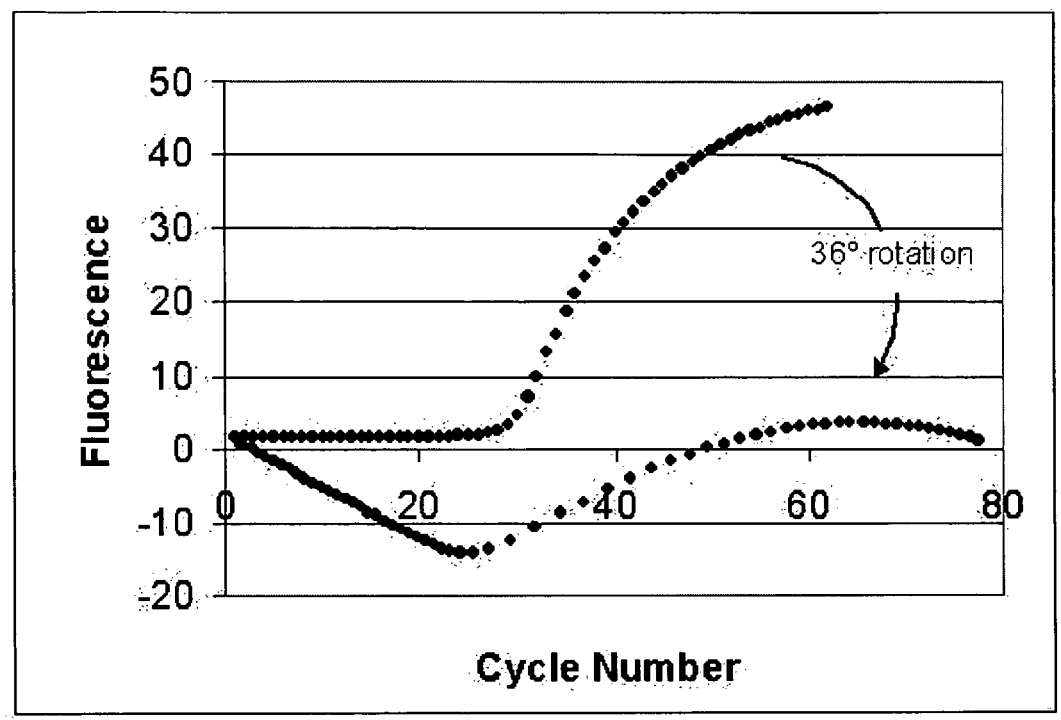
FIG. 14 shows an example of a single data set of an HCV assay plotted in a two-dimensional graph.

Kinetic PCR was performed on Hepatitis C Virus (HCV) RNA at different titer input values to produce a plurality of kinetic PCR amplification curves. Study was set up with 22 replicates each having HCV RNA titers at $10^3$, $10^4$, $10^5$, and $10^7$ c/mL and 8 replicates of negative control at 0 c/mL HCV RNA. The series of HCV amplification curves were analyzed by determining the Ct values at a rotation of 36 degrees. This angle was subjectively selected based on prior experiments. FIG. 14 shows an example of a data set of one of these assays plotted in a two-dimensional graph. At each titer value, the standard deviation of the Ct values divided by the average of the Ct values is taken. This gives the % Coefficient of Variation (% CV) value for each titer, resulting in 4% CV values (one at each titer, the 0 titer being ignored). The average of these 4% CV values is then determined. The average % CV serves as a single variable to optimize. The % CV at low titer may be more important. For example, when someone has a high amount of virus in their systems the drug dosages may be maximized. The low titer is where precision is really needed to help balance the toxicity/efficacy effect. Thus, another option is to optimize the rotation angle at the minimum titer value.

Figure 15:
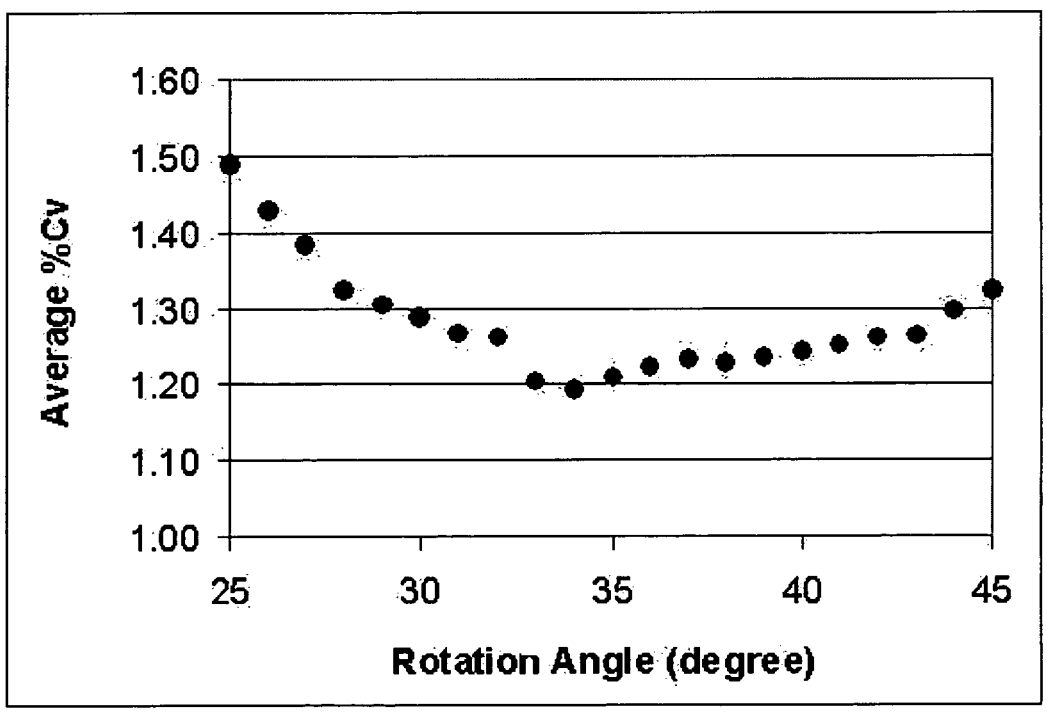
FIG. 15 shows the average Cv plotted vs. rotation angle in single increments of 1 degree for the HCV assay of FIG. 14.
Figure 16:
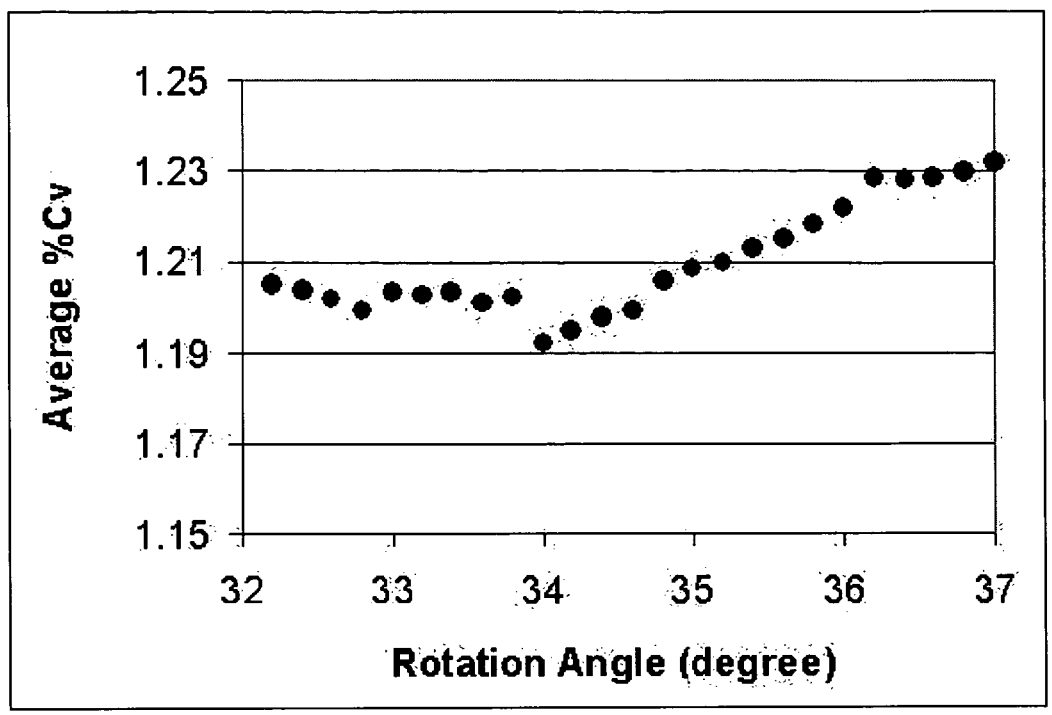
FIG. 16 shows a region from FIG. 15 expanded in increments of 0.2 degrees.

Accordingly, the analysis process is repeated at different rotation angles, for example at 1 degree increments. FIG. 15 shows the average % CV plotted vs. rotation angle in single increments of 1 degree for this HCV study. From FIG. 15, it is apparent that the minimum occurs in the region near 32-37 degrees. This region is then expanded in increments of 0.2 degrees and is plotted in FIG. 16. FIG. 16 indicates that the minimum average % CV is at 34 degrees, with a value of 1.19%, with individual values of the 4 CV of 0.97%, 0.86%, 1.4%, and 1.5%, corresponding to titers of at $10^3$, $10^4$, $10^5$, and $10^7$ c/mL, respectively.

Figure 17:
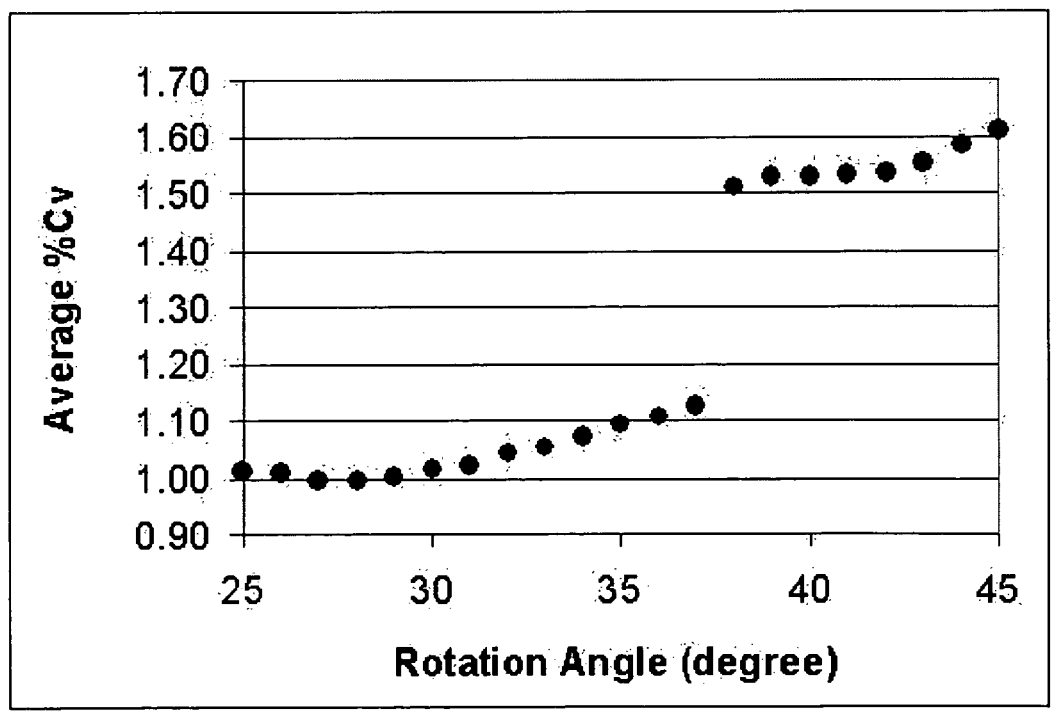
FIG. 17 shows a plot of the average Cv vs. rotation angle between 25 and 45 degrees in 1 degree increments when using normalized data for the HCV assay of FIGS. 14 and 15.
Figure 18:
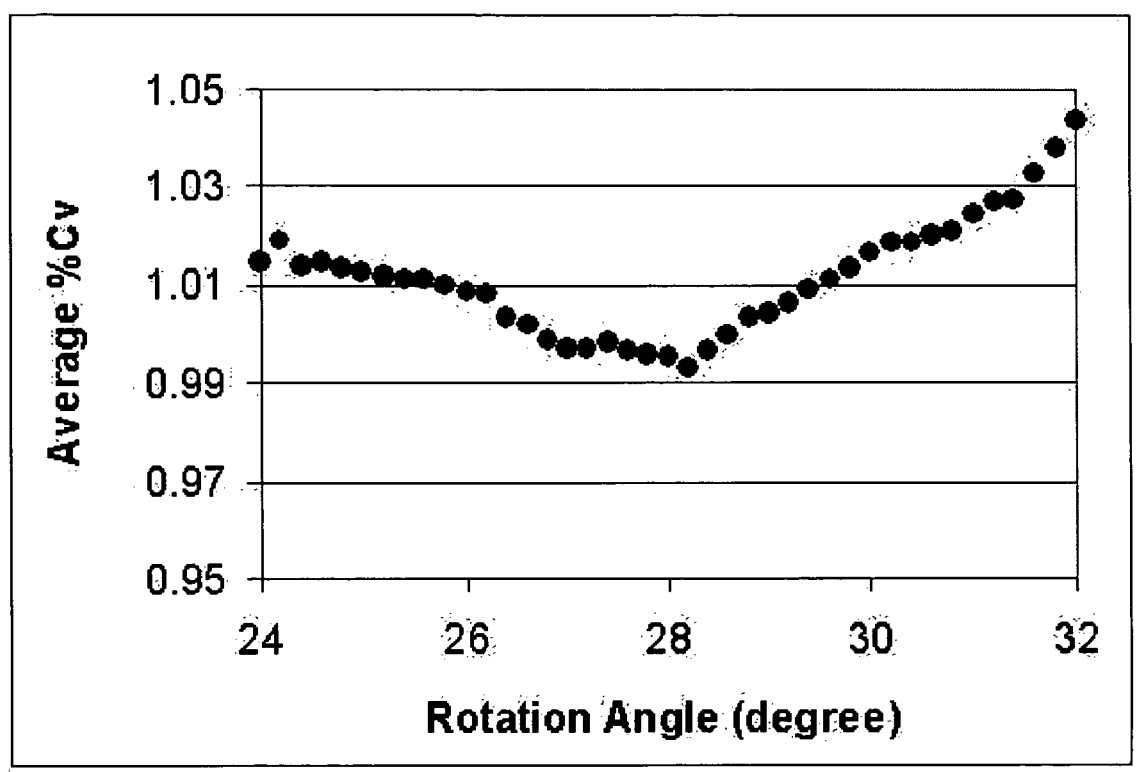
FIG. 18 shows an expansion of the data of FIG. 17 between 24-32 degrees in 0.2 degree increments.

In one aspect, the data is normalized prior to being processed through the rotational algorithm. Applying pre-rotation normalization to the HCV analysis example results in an average % CV of 0.99% and % CV values at the respective titers of 0.67%, 0.79%, 1.28%, and 1.22%. A plot of the average % CV vs. rotation angles between 25 and 45 degrees in 1 degree increments when using the normalized data is shown in FIG. 17. In this case, the minimum in the curve occurs in the range 25-35 degrees. Accordingly, FIG. 18 shows an expansion of the data between 24-32 degrees in 0.2 degree increments. As can be seen, the minimum occurs at an angle of 28.2 degrees.

It should be appreciated that other assay parameters can be utilized to optimize the rotation angle. Examples include titer precision, accuracy, and hit rate with, for example, a 95% confidence interval, minimizing the number of false positives, or minimizing the number of false negatives. It should also be appreciated that the processes described above may be implemented in a variety of analytical instruments and systems where the underlying data acquisition process may produce sigmoid curves similar to PCR amplification curves.

CONCLUSION

The fact that the minimum in a rotated data set can be determined in one aspect using a sorting method advantageously eliminates the need to take derivatives. This is an advantage as the first and especially the second derivatives that are often used in determining the elbow are extremely sensitive to noisy data. It will be appreciated, however, that other methods may be used to identify the point having the minimum (or maximum) fluorescence intensity value in the rotated data set. For example, an algorithm that searches for and locates the minimum value may be used. Useful algorithms include a method of sharpest descent algorithm, a conjugate gradient method, a Levenberg-Marquardt method and an order statistic method. These and other useful algorithms can be found in software applications such as Mathematica, or could be readily coded by one skilled in the art.

Thus, the present invention advantageously eliminates problems found in previous algorithms, for example: (1) noisy, spike data, (2) variable baselines, (3) high baselines, (4) sensitivity of derivative methods, and (5) need for a large number of parameters. The processes of the present invention are particularly useful in PCR systems, such as thermocyclers, to significantly improve the quality of the PCR results data.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, throughout the document, the rotation is described in a 2D visual graph system. However, it should be appreciated that a data set may be processed and visualized in any n-dimensional space. For example, the data may be visualized or plotted in a 3D system (e.g., with some arbitrary third dimensional coordinate), and then the rotation transforms performed with rotation around any axis or coordinate point as desired. Therefore, the scope of the appended claims should be accorded the broadest interpretation so as to encompass all such modifications and similar arrangements.

What is claimed is:

1. A computer-implemented method of determining the elbow or cycle threshold (Ct) value in a region of a Polymerase Chain Reaction (PCR) data curve, the method comprising the steps all of which are, implemented in a computer system having a processor, of:

receiving a PCR data set representing a PCR data curve, said data set including a plurality of data points each having a pair of coordinate values, wherein if viewed in a two-dimensional coordinate system the data set has a region of interest;

calculating an approximation of the PCR data curve by applying a Levenberg-Marquardt (LM) regression process to the PCR data set and a double sigmoid function to determine parameters of the function;

modifying the PCR data curve using the determined parameters to produce a modified dataset;

applying a first rotational transformation to at least a portion of the modified data set including the region of interest comprising an elbow or cycle threshold (Ct) value to produce a transformed data set;

identifying a data point in the transformed data set having at least one of a minimum coordinate value or a maximum coordinate value;

applying a second rotational transformation, inverse to the first transformation, to the identified data point; and thereafter re-determining at least one coordinate value of the identified data point, wherein the re-determined coordinate value of the identified data point represents the Ct value in the PCR data curve.

2. The method of claim 1, wherein modifying includes subtracting off a linear growth portion from the dataset.

3. The method of claim 1, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

4. The method of claim 3, wherein at least the parameters a and b are determined, and wherein modifying includes subtracting off the linear growth portion, a+bx, from the dataset.

5. The method of claim 3, wherein at least the parameters a and b are determined, and wherein modifying includes subtracting off the linear growth portion, a+bx, from the dataset and dividing the result by parameter a.

6. The method of claim 1, wherein the pair of coordinate values represents an accumulation of amplified polynucleotide and a cycle number.

7. The method of claim 1, further including interpolating additional data points using at least the data points in the region of interest.

8. The method that of claim 1, wherein the first rotational transformation rotates the coordinate values of said portion of the dataset clockwise or counterclockwise by an angle $\theta$ relative to a selected coordinate value.

9. The method of claim 8, wherein the second rotational transformation rotates the coordinate values of the first data point by an angle $-\theta$ relative to the selected coordinate value.

10. A method of claim 1, further comprising providing the Ct value as an output.

11. The method of claim 1, further comprising displaying one or both of the Ct value and the first dataset in a two dimensional coordinate system on a display device.

12. The method of claim 1, wherein identifying includes sorting the coordinate values of the data points in the transformed dataset to determine a data point having at least one minimum coordinate value or maximum coordinate value.

13. The method of claim 1, wherein identifying includes taking a derivative of the transformed dataset.

14. The method of claim 1, wherein the received dataset has been preprocessed to remove any spike points that may have been present in an original dataset.

15. A computer-implemented method of determining the cycle threshold (Ct) values for a plurality of the Polymerase Chain Reaction (PCR) curves, the method comprising the steps all of which are, implemented in a computer system having a processor, of:
receiving a plurality of datasets, each data set representing a PCR curve, each said data set including a plurality of data points each having a pair of coordinate values, wherein each said dataset includes data points in a region of interest which includes the Ct value; and
for each dataset:
calculating an approximation of the curve by applying a Levenberg-Marquardt (LM) regression process to the data set and a double sigmoid function to determine parameters of the function;
modifying the curve using the determined parameters to produce a modified dataset;
applying a first rotational transformation to at least a portion of the modified data set including the region of interest comprising an elbow or cycle threshold (Ct) value to produce a transformed data set;
identifying a data point in the transformed dataset having at least one of a minimum coordinate value or a maximum coordinate value;
applying a second rotational transformation, inverse to the first transformation, to the identified data point; and thereafter
re-determining at least one coordinate value of the identified data point, wherein the re-determined coordinate value of the identified data point represents the Ct value for the PCR curve.

16. A tangible computer-readable medium that stores code for controlling a processor to determine a cycle threshold (Ct) value in a kinetic Polymerase Chain Reaction (PCR) amplification curve, the code including instructions to:
receive a data set representing a kinetic PCR amplification curve, said data set including a plurality of data points each having a pair of coordinate values, wherein said dataset includes data points in a region of interest which includes the Ct value;
calculate an approximation of the curve by applying a Levenberg-Marquardt (LM) regression process to the data set and a double sigmoid function to determine parameters of the function;
modify the curve using the determined parameters to produce a modified dataset;
apply a first rotational transformation to at least a portion of the modified data set including the region of interest to produce a transformed data set;
identify a data point in the transformed data set having at least one of a minimum coordinate value or a maximum coordinate value;
apply a second rotational transformation, inverse to the first transformation, to the identified data point; and thereafter
re-determine at least one coordinate value of the identified data point, wherein the re-determined coordinate value of the identified data point represents the Ct value for the PCR curve.

17. A kinetic Polymerase Chain Reaction (PCR) system, comprising:
a kinetic PCR analysis module that generates a PCR data set representing a kinetic PCR amplification curve, said dataset including a plurality of data points each having a pair of coordinate values, wherein said dataset includes data points in the region of interest which includes a cycle threshold (Ct) value; and
an intelligence module adapted to process the PCR data set to determine the Ct value by:
calculating an approximation of the curve by applying a Levenberg-Marquardt (LM) regression process to the data set and a double sigmoid function to determine parameters of the function;
modifying the curve using the determined parameters to produce a modified dataset;
applying a first rotational transformation to at least a portion of the modified data set including the region of interest to produce a transformed data set;
identifying a data point in the transformed data set having at least one of a minimum coordinate value or a maximum coordinate value;
applying a second rotational transformation, inverse to the first transformation, to the identified data point; and thereafter
re-determining at least one coordinate value of the identified data point, wherein the re-determined coordinate value of the identified data point represents the Ct value for the PCR curve.

18. A Polymerase Chain Reaction (PCR) system, comprising:
a PCR data acquisition device that generates a PCR data set representing a PCR amplification curve, said dataset including a plurality of data points each having a pair of coordinate values, wherein said dataset includes data points in the region of interest which includes a cycle threshold (Ct) value; and a processor adapted to receive and to process the PCR data set to determine the Ct value by:

calculating an approximation of the curve by applying a Levenberg-Marquardt (LM) regression process to the data set and a double sigmoid function to determine parameters of the function;

modifying the curve using the determined parameters to produce a modified dataset;

applying a first rotational transformation to at least a portion of the modified data set including the region of interest to produce a transformed data set;

identifying a data point in the transformed data set having at least one of a minimum coordinate value or a maximum coordinate value;

applying a second rotational transformation, inverse to the first transformation, to the identified data point; and thereafter re-determining at least one coordinate value of the identified data point, wherein the re-determined coordinate value of the identified data point represents the Ct value for the PCR curve.

* * * * *